United States Patent
Pham-Huu et al.

(10) Patent No.: US 10,682,633 B2
(45) Date of Patent: Jun. 16, 2020

(54) METHOD FOR PREPARING HIGHLY NITROGEN-DOPED MESOPOROUS CARBON COMPOSITES

(71) Applicants: UNIVERSITÉ DE STRASBOURG, Strasbourg (FR); CENTRE NATIONAL DE LA RECHERCHE SCIENTIFIQUE, Paris (FR); CONSIGLIO NAZIONALE DELLE RICERCHE, Rome (IT)

(72) Inventors: Cuong Pham-Huu, Strasbourg (FR); Giuliano Giambastiani, Florence (IT); Yuefeng Liu, Strasbourg (FR); Housseinou Ba, Strasbourg (FR); Lam Nguyen-Dinh, Da-Nang (VN); Jean-Mario Nhut, Plobsheim (FR); Cuong Duong-Viet, Strasbourg (FR)

(73) Assignees: UNIVERSITÉDE STRASBOURG, Strasbourg (FR); CENTRE NATIONAL DE LA RECHERCHE SCIENTIFIQUE, Paris (FR); CONSIGLIO NAZIONALE DELLE RICERCHE, Rome (IT)

( * ) Notice: Subject to any disclaimer, the term of this patent is extended or adjusted under 35 U.S.C. 154(b) by 153 days.

(21) Appl. No.: 15/545,536

(22) PCT Filed: Jan. 21, 2016

(86) PCT No.: PCT/EP2016/051196
§ 371 (c)(1),
(2) Date: Jul. 21, 2017

(87) PCT Pub. No.: WO2016/116542
PCT Pub. Date: Jul. 28, 2016

(65) Prior Publication Data
US 2018/0008968 A1    Jan. 11, 2018

(30) Foreign Application Priority Data

Jan. 21, 2015 (EP) .................... 15152038
Jan. 21, 2015 (EP) .................... 15152039

(51) Int. Cl.
| | | |
|---|---|---|
| B01J 20/20 | (2006.01) | |
| B01J 27/24 | (2006.01) | |
| B01J 21/04 | (2006.01) | |
| B01J 27/224 | (2006.01) | |
| H01M 4/96 | (2006.01) | |
| B01J 27/20 | (2006.01) | |
| B01J 37/02 | (2006.01) | |
| B01J 21/18 | (2006.01) | |
| B01J 35/00 | (2006.01) | |
| B01J 35/02 | (2006.01) | |
| B01J 35/10 | (2006.01) | |
| B01J 37/04 | (2006.01) | |
| C01B 17/04 | (2006.01) | |
| C07C 5/333 | (2006.01) | |

(52) U.S. Cl.
CPC ............... *B01J 27/24* (2013.01); *B01J 20/20* (2013.01); *B01J 21/04* (2013.01); *B01J 21/18* (2013.01); *B01J 27/20* (2013.01); *B01J 27/224* (2013.01); *B01J 35/0006* (2013.01); *B01J 35/026* (2013.01); *B01J 35/1061* (2013.01); *B01J 37/0203* (2013.01); *B01J 37/0217* (2013.01); *B01J 37/0221* (2013.01); *B01J 37/0236* (2013.01); *B01J 37/0244* (2013.01); *B01J 37/04* (2013.01); *C01B 17/0465* (2013.01); *C07C 5/333* (2013.01); *H01M 4/96* (2013.01); *C07C 2521/04* (2013.01); *C07C 2527/224* (2013.01); *C07C 2527/24* (2013.01)

(58) Field of Classification Search
CPC ....................................................... B01J 20/20
See application file for complete search history.

(56) References Cited

FOREIGN PATENT DOCUMENTS

| | | |
|---|---|---|
| CN | 103706388 A | 4/2014 |
| CN | 103723716 A | 4/2014 |
| EP | 1941946 A1 | 7/2008 |
| JP | 2009-48867 A | 3/2009 |
| JP | 2010-509174 A | 3/2010 |
| JP | 2011-195351 A | 10/2011 |
| WO | WO2008058231 A2 | 5/2008 |

OTHER PUBLICATIONS

Kuo, P.-L., et al., "Controllable-Nitrogen Doped Carbon Layer Surrounding Carbon Nanotubes as Novel Carbon Support for Oxygen Reduction Reaction," Fuel Cells 2012;12(4):649-655.

An, B., et al., "Carbon nanotubes coated with a nitrogen-doped carbon layer and its enhanced electrochemical capacitance," J. Materials Chem. A 2013;1(24):7222, Abstract only.

Hsu, C.-H., et al., "The use of carbon nanotubes coated with a porous nitrogen-doped carbon layer with embedded Pt for the methanol oxidation reaction," J. Power Sources 2011;198:83-89, Abstract only.

Rongfang, W., et al., "Nitrogen-droped carbon coated Zr02as a support for Pt nanoparticles in the oxygen reduction reaction," Int. J. Hydrogen Energy 2013;38(14):5783-5788.

(Continued)

*Primary Examiner* — Stuart L Hendrickson
(74) *Attorney, Agent, or Firm* — Kenealy Vaidya LLP

(57) ABSTRACT

Some embodiments are directed to a new methodology aimed at preparing highly N-doped mesoporous carbon macroscopic composites, and their use as highly efficient heterogeneous metal-free catalysts in a number of industrially relevant catalytic transformations.

11 Claims, 8 Drawing Sheets

(56) References Cited

OTHER PUBLICATIONS

Dante, R. C., et al., "Synthesis of graphitic carbon nitride by reaction of melamine and uric acid," Materials Chem. Phys. 2011;130(3):1094-1102.

Thomas, A., et al., "Graphitic carbon nitride materials: variation of structure and morphology and their use as metal-free catalysts," J. Materials Chem. 2008;18(41):4893, Abstract only.

Chizari, K., et al., "Nitrogen-Doped Carbon Nanotubes as a Highly Active Metal-Free Catalyst for Selective Oxidation," Chemsuschem 2012;5(1):102-108.

International Search Report for PCT Patent App. No. PCT/EP2016/051196 dated Apr. 1, 2016.

Written Opinion for PCT Patent App. No. PCT/EP2016/051196 dated Apr. 1, 2016.

K. P. Gong, F. Du, Z. H. Xia, M. Durstock, L. M. Dai, Nitrogen-Doped Carbon Nanotube Arrays with High Electrocatalytic Activity for Oxygen Reduction. Science 323, 760-764 (2009).

Y. G. Li et al., An oxygen reduction electrocatalyst based on carbon nanotube-graphene complexes. Nat Nanotechnol 7, 394-400 (2012).

R. L. Liu, D. Q. Wu, X. L. Feng, K. Mullen, Nitrogen-Doped Ordered Mesoporous Graphitic Arrays with High Electrocatalytic Activity for Oxygen Reduction. Angew Chem Int Edit 49, 2565-2569 (2010).

K. Chizari et al., Nitrogen-Doped Carbon Nanotubes as a Highly Active Metal-Free Catalyst for Selective Oxidation. Chemsuschem 5, 102-108 (2012).

D. S. Su, S. Perathoner, G. Centi, Nanocarbons for the Development of Advanced Catalysts. Chemical Reviews 113, 5782-5816 (2013).

C. W. Zhou, J. Kong, E. Yenilmez, H. J. Dai, Modulated chemical doping of individual carbon nanotubes. Science 290, 1552-1555 (2000).

X. R. Wang et al., N-Doping of Graphene Through Electrothermal Reactions with Ammonia. Science 324, 768-771 (2009).

S. G. Zhang, M. S. Miran, A. Ikoma, K. Dokko, M. Watanabe, Protic Ionic Liquids and Salts as Versatile Carbon Precursors. J Am Chem Soc 136, 1690-1693 (2014).

X. H. Li, M. Antonietti, Polycondensation of Boron- and Nitrogen-Codoped Holey Graphene Monoliths from Molecules: Carbocatalysts for Selective Oxidation. Angew Chem Int Ed 52, 4572-4576 (2013).

J. Liang, X. Du, C. Gibson, X. W. Du, S. Z. Qiao, N-Doped Graphene Natively Grown on Hierarchical Ordered Porous Carbon for Enhanced Oxygen Reduction. Adv Mater 25, 6226-6231 (2013).

H. G. Wang et al., Nitrogen-Doped Porous Carbon Nanosheets as Low-Cost, High-Performance Anode Material for Sodium-Ion Batteries. Chemsuschem 6, 56-60 (2013).

L. T. Qu, Y. Liu, J. B. Baek, L. M. Dai, Nitrogen-Doped Graphene as Efficient Metal-Free Electrocatalyst for Oxygen Reduction in Fuel Cells. ACS Nano 4, 1321-1326 (2010).

X. Y. Li et al., Silicon carbide-derived carbon nanocomposite as a substitute for mercury in the catalytic hydrochlorination of acetylene. Nat Commun 5, (2014).

Y. Zhao, R. Nakamura, K. Kamiya, S. Nakanishi, K. Hashimoto, Nitrogen-doped carbon nanomaterials as non-metal electrocatalysts for water oxidation. Nat Commun 4, art. 2390, (2013).

P. Nguyen et al., High thermal conductive beta-SiC for selective oxidation of H2S: A new support for exothermal reactions. Appl Catal B-Environ 76, 300-310 (2007).

J. A. Zhang et al., Surface Chemistry and Catalytic Reactivity of a Nanodiamond in the Steam-Free Dehydrogenation of Ethylbenzene. Angew Chem Int Edit 49, 8640-8644 (2010).

J. Chlistunoff, RRDE and Voltammetric Study of ORR on Pyrolyzed Fe/Polyaniline Catalyst. On the Origins of Variable Tafel Slopes. J Phys Chem C 115, 6496-6507 (2011).

M.-M. Titirici, R. J. White, C. Falco, M. Sevilla, Black perspectives for a green future: hydrothermal carbons for environment protection and energy storage. Energy Environ Sci 5, 6796-6822 (2012).

C. O. Tuck, E. Perez, I. T. Horvath, R. A. Sheldon, M. Poliakoff, Valorization of Biomass: Deriving More Value from Waste. Science 337, 695-699 (2012).

D. Y. Zhang, Y. Hao, Y. Ma, H. X. Feng, Hydrothermal synthesis of highly nitrogen-doped carbon powder. Appl Surf Sci 258, 2510-2514 (2012).

K. G. Latham, G. Jambu, S. D. Joseph, S. W. Donne, Nitrogen Doping of Hydrochars Produced Hydrothermal Treatment of Sucrose in H2O, H2SO4, and NaOH. ACS Sustain Chem Eng 2, 755-764 (2014).

F. W. Lichtenthaler, A. Brust, E. Cuny, Sugar-derived building blocks. Part 26. Hydrophilic pyrroles, pyridazines and diazepinones from D-fructose and isomaltulose. Green Chem 3, 201-209 (2001).

F. W. Lichtenthaler, Unsaturated O- and N-heterocycles from carbohydrate feedstocks. Accounts Chem Res 35, 728-737 (2002).

Yang et al. "The Correlation of Interfacial Interaction and Catalytic Performance of N-Doped Mesoporous Carbon Supported Cobalt Nanoparticles for Fischer-Tropsch Synthesis", The Journal of Physical Chemistry C, Dec. 9, 2013, vol. 118, p. 268-277.

Office Action dated Sep. 23, 2019 to Chinese patent application No. 201680006434.X.

Office Action dated Oct. 8, 2019 to Japanese patent application No. 2017-539024.

METHOD FOR PREPARING HIGHLY NITROGEN-DOPED MESOPOROUS CARBON COMPOSITES

CROSS REFERENCE TO RELATED APPLICATIONS

This application is a National Phase filing under 35 C.F.R. § 371 of and claims relatedity to PCT Patent Application No.: PCT/EP2016/051196, filed on Jan. 21, 2016, which claims priority to European Patent Application No. EP 15152038.4, and provisional European Patent Application No. EP 15152039.2, both filed on 21 Jan. 2015, the entire contents of which are hereby incorporated by reference in their entireties.

BACKGROUND

Some embodiments are directed to a new methodology aimed at preparing highly nitrogen-doped mesoporous carbon macroscopic composites, and their use as highly efficient heterogeneous metal-free catalysts in a number of industrially relevant catalytic transformations.

In this document, the numbers in italics and between brackets ( ) refer to the List of References given at the end of the document.

Re-thinking fundamental metal-based catalytic processes, in the light of tailored metal-free catalytic architectures, designed and fabricated from cheap and easily accessible building blocks, represent a challenging matter of the modern and really sustainable catalysis. Nitrogen-doped 1D and 2D carbon nanomaterials (N-CNMs) have emerged in the last decade as effective metal-free systems capable to promote efficiently a high number of catalytic processes (1-5). Recent studies have demonstrated how the inclusion of nitrogen(s) in the honeycomb carbon structure, breaks the electroneutrality of the $C_{sp2}$ network (6, 7) and generates charged sites, with improved reagent's adsorption properties, capable to foster several catalytic transformations. Among the methods used for N-CNMs synthesis, the Chemical Vapor Deposition (CVD) still remains the most effective and widely used technique; other approaches like the annealing of CNMs in the presence of different nitrogen sources and the direct carbonization of N-containing organic precursors (3, 8) constitute valuable and alternative synthetic paths. At odds with the feasibility of these methods, nitrogen precursors with relatively high toxicity, i.e. dicyandiamide (9), melamine (10), polypyrrole (11), ammonia (12, 13, 14) along with generally high operation temperatures, under hydrocarbons and hydrogen atmosphere, are normally required to get the final N-doped materials. In addition, the low efficiency of these synthetic protocols generally results into a significant loss of the nitrogen and carbon precursors used, which calls for an extensive recycling of the exit gaseous reactants. Moreover, the harsh reaction conditions required to get N-CNMs are generally responsible for the generation of many waste by-products and for the growing process costs. Last but not least, many nitrogen precursors are relatively toxic compounds which often necessitate of specific precaution for their appropriate handling and processing. Alternative approaches to the N-decoration of CNMs, like the milder chemical functionalization of nanocarbon sidewalls and tips, have recently gain interest as an ideal paradigm for getting new insights on the role of N-functionalities as well as that of their chemical environment in specific catalytic transformations. In spite of their remarkable catalytic performance, these materials suffer of several limitations: from a high temperature sensitivity (that makes them ideal for low- or medium-temperature catalytic processes only) to severe synthetic restrictions (i.e. tricky upscale procedures and difficult material handling because of their powdery texture).

Therefore, there remains a need to overcome the main disadvantages known in the art and to devise a more straightforward and environmentally friendly synthetic methodology for the preparation of highly N-doped carbon-based materials. In particular, their achievement in the form of "highly flexible" coatings for a variety of macroscopic supports, thereby allowing access to a wide variety of composite materials for use as effective metal-free and environmentally friendly heterogeneous catalysts, still remain a challenging target for addressing a number of industrially relevant catalytic transformations.

Definitions

As used herein, the term "macroscopic", when referring for example to a material, a support or a catalyst, or assembly thereof, means "macroscopic-sized" within the conventional meaning of the term in the art. For example, as used herein "macroscopic material" or "macroscopic support" refers to a material or support that is in the range of few tenths of μm (≥0.1 μm) up to tenths of cm or more (≤100 cm) in three orthogonal directions. In some cases the support can also involve nanostructured materials with smaller dimension, i.e. <0.1 μm. In such a case the term "macroscopic" when referring for example to a support, will refer to the final assembly of these nanostructured materials into a macroscopic support for subsequent downstream applications. In all cases, the final macroscopic support/material/catalyst will have a dimension ≥0.1 μm. For example, macroscopic materials, supports or catalysts within the meaning of the present invention may range in size from 10 μm to 90 cm in three orthogonal directions. The macroscopic material or support can be in the form of discrete objects, like grains, flakes, rings, pellets, extrudates, beads or foams. Alternatively, it can be a macroscopic assembly of smaller objects. Likewise, a "macroscopic assembly of smaller objects" within the meaning of the invention refers to an assembly (of smaller objects) whose size ranges between a few tenths of μm (≥0.1 μm) up to tenths of cm or more (≤100 cm) in three orthogonal directions. For example, a macroscopic material can be composed of carbon nanotubes and it can be obtained by: (1) randomly aligned, isotropic ensemble of entangled nanotubes without requiring nanotube-nanotube junctions; (2) randomly aligned isotropic ensemble or an ordered array nanotube structure containing two-dimensional nanotube junctions; (3) randomly aligned isotropic ensemble or an ordered array nanotube structure containing three-dimensional nanotube junctions; (4) a structure composed of any combination of (1), (2) and (3). As further used herein, a "junction" is considered to be any form of bonding (covalent or non-covalent) between the nanotubes at any (all) angle(s). As further used herein, a "two-dimensional nanotube junction" refers to a nanotube that is a least 100 nm in two perpendicular directions (or in the same 2D plane having any angle), while, in the direction orthogonal to both perpendicular directions (2D plane), the nanotube is generally less than 100 nm. Likewise, a "three-dimensional nanotube junction" refers to a nanotube that is a least 100 nm in three orthogonal directions.

As used herein, with respect to doping with nitrogen atoms, the term "doping" refers to placing nitrogen atoms in the carbon atom lattice in place of carbon atoms. For example a "N-doped CNT" is a carbon nanotube that has "implanted" nitrogen atoms replacing carbon atoms in the CNT lattice.

As used herein, the abbreviation "N@C" refers to the N-doped mesoporous carbon structure as will be described below. The macroscopic supports coated/decorated with the N@C layer will be abbreviated/referred to herein as "macroscopic composites" or "macroscopic catalysts".

SUMMARY

As noted above, recent years have witnessed a growing interest in the development of new synthetic methods aimed at preparing highly N-doped carbon composite materials and their subsequent application as metal-free systems in several catalytic processes.

In this context, there is provided herein a novel method of preparing macroscopic composites made of a macroscopic support (host matrix) coated with a thin layer of highly nitrogen-doped mesoporous carbon phase (active phase), said method comprising:
  (a) providing an aqueous solution of (i) $(NH_4)_2CO_3$, (ii) a carbohydrate as carbon source, selected from aldose monosaccharides and glycosilated forms thereof, disaccharides and oligosaccharides, and (iii) a carboxylic acid source selected from citric acid, and any other mono-, di-, tri-, and poly-carboxylic acid or their ammonium mono-, di-, tri- and poly-basic forms;
  (b) providing a macroscopic support made of carbon-, silicium- or aluminum-based material, or binary mixtures thereof;
  (c) immerging/soaking or impregnating the macroscopic support of step (b) in the aqueous solution of step (a) for a suitable amount of time;
  (d) optionally removing the immerged macroscopic support from the aqueous solution if an excess aqueous solution is used in step (c);
  (e) subjecting the resulting macroscopic support to a first thermal treatment (drying) under air at moderate temperatures from 110-150° C.±5° C., preferably 130° C.±5° C.; and
  (f) subjecting the thermally treated (dried) macroscopic support to a second thermal treatment under air at higher temperatures from 400-500° C.±10° C., preferably 450° C.±5° C., most preferably 400° C.±5° C.; thereby generating a macroscopic composite composed of a macroscopic support coated with a thin layer of highly N-doped mesoporous carbonaceous material; and
  (g) optionally subjecting the macroscopic composite obtained in step (f) to a third thermal treatment by heating it to a temperature ranging between 600 to 900° C.±10° C. under inert atmosphere, preferably 700 to 900° C.±10° C., or 700 to 800° C.±10° C.

Advantageously, when carrying out step (g), the treatment temperature (i.e., 600 to 900° C.±10° C. under inert atmosphere, preferably 700 to 900° C.±10° C., or 700 to 800° C.±10° C.) is reached progressively, for example via a linear heating up-ramp. For example, a heating rate of 10° C./min may be used to reach the treatment temperature of step (g).

In a variant, the method may further comprise a step (e'), between steps (d) and (e), of gentle drying the macroscopic support resulting for step (d). Advantageously, this gentle drying step may be carried out under air at low temperatures from 45 to 55° C., preferably 50° C.±3° C.

In a variant, step (f) may be carried out under air at 300° C.±10° C. for a longer period of time than when a higher temperature of 400-500° C.±10° C., preferably 450° C.±5° C., most preferably 400° C.±5° C., is used.

In a variant, the method may further comprise subjecting the macroscopic support of step (b) to a passivation process comprising steps of:
  (c1) prior to step (c), coating the macroscopic support of step (b) with a carbon source;
  (e1) subjecting the resulting macroscopic support to a first thermal treatment (drying) under air at moderate temperatures from 110-150° C.±5° C., preferably 130° C.±5° C.; and
  (f1) subjecting the thermally treated (dried) macroscopic support to a second thermal treatment under inert atmosphere at higher temperatures from 600-800° C.±10° C., preferably 600° C.±5° C.; thereby generating a macroscopic composite coated with a carbon layer.

The carbon source used in the passivation process may be any suitable carbon source which, upon thermal treatments (e1) and (f1), can produce a carbon layer. For example, the carbon source may be a phenolic resin, polyacrylonitrile (PAN), or the like. The carbon source may also be a carbohydrate, selected from aldose monosaccharides and glycosilated forms thereof, disaccharides and oligosaccharides, in the presence of a carboxylic acid, such as citric acid, which participates in the carbohydrate polymerization.

As such, the method may further comprise subjecting the macroscopic support of step (b) to a passivation process comprising steps of:
  (a1) providing an aqueous solution of citric acid and a carbohydrate as carbon source, selected from aldose monosaccharides and glycosilated forms thereof, disaccharides and oligosaccharides;
  (c1) prior to step (c), immerging/soaking or impregnating the macroscopic support of step (b) in the aqueous solution of step (a1) for a suitable amount of time;
  (d1) optionally removing the immerged macroscopic support from the aqueous solution of step (a1) if an excess aqueous solution is used in step (c1);
  (e1') optionally subjecting the resulting macroscopic support to a gentle thermal treatment (drying) under air at low temperatures from 45 to 55° C., preferably 50° C.±3° C.;
  (e1) subjecting the resulting macroscopic support to a first thermal treatment (drying) under air at moderate temperatures from 110-150° C.±5° C., preferably 130° C.±5° C.; and
  (f1) subjecting the thermally treated (dried) macroscopic support to a second thermal treatment under inert atmosphere at higher temperatures from 600-800° C.±10° C., preferably 600° C.±5° C.; thereby generating a macroscopic composite coated with a carbon layer.

The passivated macroscopic support obtained in step (f1) may be immerged/soaked or impregnated according to step (c). Preferably, the passivated macroscopic support obtained in step (f1) is cooled to room temperature (25° C.) prior to subjecting it to step (c).

Advantageously, the passivation process is carried out when the macroscopic support is silica ($SiO_2$), alumina ($Al_2O_3$) or titania ($TiO_2$); preferably silica ($SiO_2$) or alumina ($Al_2O_3$). The passivation process allows to coat the macroscopic support with a carbon layer prior to coating it with the N-doped mesoporous carbonaceous layer. The intermediate carbon layer allows to reduce the chemical interactions between the N-doped mesoporous carbonaceous and the support and to enhance the adhesion of the N-doped mesoporous carbonaceous layer on the macroscopic support. This is particularly useful when the macroscopic support is not made of a C-containing material, for example when the macroscopic support is a silica ($SiO_2$), alumina ($Al_2O_3$) or titania ($TiO_2$); preferably silica ($SiO_2$) or alumina ($Al_2O_3$) support.

In a variant, the method may omit step (f) in favour of step (g). As such, in this "step (f)-free" variant, there is provided a method of preparing macroscopic composites made of a macroscopic support (host matrix) coated with a thin layer of highly nitrogen-doped mesoporous carbon phase (active phase), said method comprising:
- (a) providing an aqueous solution of (i) $(NH_4)_2CO_3$, (ii) a carbohydrate as carbon source, selected from aldose monosaccharides and glycosilated forms thereof, disaccharides and oligosaccharides, and (iii) a carboxylic acid source selected from citric acid, and any other mono-, di-, tri-, and poly-carboxylic acid or their ammonium mono-, di-, tri- and poly-basic forms;
- (b) providing a macroscopic support made of carbon-, silicium- or aluminum-based material, or binary mixtures thereof;
- (c) immerging/soaking or impregnating the macroscopic support of step (b) in the aqueous solution of step (a) for a suitable amount of time;
- (d) optionally removing the immerged macroscopic support from the aqueous solution if an excess aqueous solution is used in step (c);
- (e) subjecting the resulting macroscopic support to a first thermal treatment (drying) under air at moderate temperatures from 110-150° C.±5° C., preferably 130° C.±5° C.; and
- (g) subjecting the macroscopic composite obtained in step (e) to a third thermal treatment by heating it to a temperature ranging between 600 to 900° C.±10° C. under inert atmosphere, preferably 700 to 900° C.±10° C., or 700 to 800° C.±10° C.

All other variant described above (e.g., additional step (e'), passivation process), are also applicable to the present "step (f)-free" variant. In such variant, the removal of step (f) results in the coating the macroscopic support with more N-doped carbon phase, since during step (f), part of the carbon precursor is removed through reaction with oxygen. In other words, by removing step (f), less carbon precursor is removed by thermal treatment, and therefore more N-doped carbon phase coats the macroscopic support. The composite obtained by such "step (0-free" variant typically displays a high desulfurization activity, in terms of $H_2S$ conversion, along with medium to high sulfur selectivity, i.e. 60 to >80%.

As used herein the term "thin layer" when referring to a macroscopic support (host matrix) coated with a highly nitrogen-doped mesoporous carbon phase (active phase), prepared according to the process of the invention, refers to a layer of thickness in the range of 5 to 200±5 nm, preferably 10 to 100±5 nm. The thickness of the N-doped carbon layer can be measured by means of an Energy filtered TEM (EFTEM).

As used herein the term "mesoporous", when referring to a macroscopic support (host matrix) coated with a highly nitrogen-doped mesoporous carbon phase (active phase), prepared according to the process of the invention, refers to a porous N-doped carbon phase where the average size of the pores is in the mesoporous range (2-50 nm). Typically, most of the pores are in the mesoporous range, but the presence of micropores is not excluded, though such micropores remain scarce.

The carbon phase porosity may be determined from the Brunauer-Emmett-Teller (BET) specific surface area (SSA) based on either BJH and t-plot methods using conventional equipment. For example, the BET and porosity (based on either BJH and t-plot methods) can be measured on an ASAP 2020 Micromeritics instrument, using $N_2$ as absorbent at the liquid $N_2$ temperature. All samples were completely degassed/activated at 250° C. for 14 h.

The carbohydrate carbon source may be selected from the simplest aldose monosaccharides like glucose, maltose, lactose, including their glycosilated forms, up to more complex disaccharides like saccharose and oligosaccharides or dextrine deriving from biomass conversion.

The carboxylic acid source may be selected from citric acid, and any other mono-, di-, tri-, and poly-carboxylic acid or their ammonium mono-, di-, tri- and poly-basic forms like ammonium citric acid mono-basic, ammonium citric acid di-basic and ammonium citric acid tri-basic.

The macroscopic support can be made of carbon-based materials such as carbon nanotubes, carbon nanofibers, graphene and few-layer graphene, etc. It can be also made of silicon-based materials such as silicon carbide (alpha- and beta-SiC or related SiC-based supports, either pure or doped with foreign elements such as $TiO_2$, $Al_2O_3$, $SiO_2$), silica, etc. It also can be made of aluminum-based materials such as alumina (α- or β-$Al_2O_3$ or related alumina-based supports, either pure or doped with foreign elements such as $TiO_2$, $SiO_2$ . . . etc). The macroscopic material can also have a binary composition, such as SiC—$Al_2O_3$, SiC-silica, SiC-carbon, etc., and it can also be doped with different metal or metal-oxide dopants, such as $TiO_2$.

Advantageously, the macroscopic support may be selected from the assembly of carbon nanotubes and/or graphene (single graphene sheets, few-layer graphene sheets or graphene flakes); alpha- and beta-SiC or related SiC-based supports, either pure or doped with foreign elements such as $TiO_2$, $Al_2O_3$, $SiO_2$ . . . , in the form of grains, pellets, rings, foams, etc.; alumina (α and β structure or related alumina-based supports, either pure or doped with foreign elements such as $TiO_2$, $SiO_2$ . . . ) in the form of grains, pellets, rings, beads and foams, etc.; carbon in the form of grains, pellets, rings, beads and foam, etc.; silica in the form of grains, pellets, rings, beads, etc. The macroscopic supports could also be prepared from a binary mixture of the different supports described above. The macroscopic supports can be in any known form available in the art, for example grains, pellets, rings, foams, etc.

Advantageously, the macroscopic support may be silica ($SiO_2$), alumina ($Al_2O_3$) or titania ($TiO_2$); preferably silica ($SiO_2$), SiC or alumina ($Al_2O_3$).

Advantageously, the macroscopic support may be in the form of grains, flakes, rings, pellets, extrudates, beads or foams, which are the most usual macroscopic forms used in industrial plants. In that case, the immerging step (c) may be referred to as "impregnating" to reflect the fact that the macroscopic support soaks up aqueous solution of step (a) into its pores and/or recesses. The support can be also directly impregnated by a mixture solution through a drop-wise process. Advantageously, the supports should display an adequate porous network, preferentially meso to macropores in order to reduce as much as possible the problem of diffusion as well pore-plugging consecutive to the carbon deposit.

In step (c), the support can be impregnated with an appropriate amount of solution followed by thermal treatments as described in steps (e), (f) and (g). Impregnation can take place when the macroscopic support is porous or it is structured in such a way that it is amenable to being loaded up with the solution obtained in step (a) by capilarity effect.

Alternatively, in step (c), the support can be impregnated by the method of pore-volume impregnation. As used herein "pore-volume impregnation" refers to the use of a liquid volume equal to the pore volume of the macroscopic support. This can be achieved by measuring the volume of the liquid necessary to fill up the pore volume of the macroscopic support, usually the liquid is water taken into account that the support displays hydrophilic character. In the case of hydrophobic character the volume titrate liquid can be chosen among alcohols or organic solvents. The aqueous solution of step (a) may then be prepared within this determined volume and the solution will be further used to impregnate the support.

The nitrogen content in the macroscopic support coating, and the coating thickness, can be tuned by repeating the immerging/soaking/impregnating step and the first thermal treatment steps [from steps (c) to step (f)] as many times as needed to reach the desired nitrogen content and coating thickness, or the upper nitrogen content limit achievable, prior to carrying out the higher temperature thermal treatment step (g). As such, steps (c) through (f) may be repeated at least once prior to carrying out step (g). Advantageously, steps (c-f) may be repeated 1, 2, 3, 4, 5, 6, 7, 8, 9 or 10 times, preferably 1 to 3 times, prior to carrying out step (g). When steps (c) through (f) are repeated, the concentration of the aqueous solution used in the repeated immerging/soaking/impregnating steps (c) may be the same or different.

As used herein the term "highly nitrogen-doped" when referring to a macroscopic support (host matrix) coated with a highly nitrogen-doped mesoporous carbon phase (active phase), prepared according to the process of the invention, refers to a mesoporous N-doped carbon phase where the N atom % is 1-40%, preferably 5-40%, preferably 10-40%, preferably about 15% (e.g., 12-18%) with respect to other atoms present in the N-doped carbon phase. Typically these other atoms are carbon atoms. However, the N-doped carbonaceous phase sometimes contains also a small amount of oxygen atoms, generally attached to both carbon and nitrogen atoms. The content in oxygen atoms can vary from 2 to 6%. The N atom % in the N-doped carbon phase coating the macroscopic support will depend on the temperature of the various thermal treatments applied through the method of the present invention, specifically the temperatures used in steps (f) and (g). The higher the temperature, the lower the N atom % in the N-doped carbon phase. Generally, step (f) involves lower treatment temperatures than step (g). As such, the N-doped carbon phase obtained after step (f) will generally have a greater N atom % than the N-doped carbon phase obtained after step (g). As used herein, "highly nitrogen-doped mesoporous carbon phase" excludes a mesoporous carbonitride phase. The N atom % may be measured by either X-ray Photoelectron Spectroscopy (XPS) or elemental analysis.

The XPS technique provides the N atom % concentration on the surface of the mesoporous carbonaceous layer coating the macroscopic support (analysis of thickness not exceeding 9 nm). Whereas elemental analysis provides the N atom % concentration in the whole volume of the mesoporous carbonaceous layer coating the macroscopic support. Nevertheless, each of these two techniques may be used to determine the N atom %. For purposes of the present invention, preferably, XPS is used to measure the N atom %. Throughout this document, the recited N atom % are based on XPS analysis.

In general, the graphitization step (g) results in a decrease in N atom % in the carbonaceous layer as compared to the N atom % obtained after step (f), in part due to the lost of weakly adsorbed nitrogen species. As such, after step (f) the N-doped carbonaceous layer may have a N atom % in the range of 25-40%. If step (g) is carried out, the N-doped carbonaceous layer may have a N atom % in the range of 2-35%, preferably 5-30%, most preferably about 15% (10-20%, preferably 12-18%). A graphitization temperature in the lower range (e.g., 700° C.±10° C.) may lead to N atom % in the higher range (for example 15-30%, most preferably about 20% (18-25%)). Conversely, a graphitization temperature in the higher range (e.g., 900° C.±10° C.) may lead to N atom % in the lower range (for example 5-10%).

The nitrogen content may also be controlled by tuning the ammonium carbonate (($NH_4$)$_2CO_3$)/carbohydrate/carboxylic acid source molar ratio, preferably the ammonium carbonate/carbohydrate/citric acid molar ratio, in the aqueous solution. For example, when citric acid is used as the carboxylic acid source, the ammonium carbonate/carbohydrate/citric acid molar ratio may range from 1/1/1 to 8/5/3 mol/L, preferably from 2/2/2 to 6/4/3 mol/L.

The nitrogen range can be also finely turned by applying an appropriate thermal treatment, i.e. (f) and (g), (f) only, or (g) only.

The presence of a nitrogen-doped carbon layer on the macroscopic support significantly changes the surface properties of the final macroscopic composite (or catalyst). The N-sites are readily available at the outmost surface of the macroscopic composite (or catalyst) and they are available for chemical reactions, preferentially catalytic reactions, to take place. As a matter of fact, the N-doped carbon layer enhances remarkably the reactivity of the ultimate macroscopic composite (or catalyst) system, in particular, towards catalytic transformations occurring at the composite surface.

Depending on the application for which the final product is intended (e.g., the intended downstream catalytic applications), a third thermal treatment step (g) may be carried out in the form of a graphitization process under inert atmosphere at higher temperature, such as 700-1000° C.±20° C., preferably 600 to 900° C.±10° C., preferably 700 to 800° C., most preferably 700 to 900° C.±10° C. The temperature range will depend on the type of macroscopic support employed. Preferably, the temperature should not exceed the temperature at which the macroscopic support starts undergoing decomposition. Advantageously, the macroscopic supports used in the method of the invention have a relatively high thermal stability far beyond the operated temperature used (e.g., SiC- and carbon-based materials which decompose well beyond the operation temperatures used in the context of the present invention). In addition, the thermal treatment temperature should preferably not induce any chemical reaction between the active phase (N-doped mesoporous carbonaceous layer) and the macroscopic support. In the case where some chemical interactions should take place, e.g. silica, titania and alumina macroscopic supports, a passivated carbon layer could be implemented (passivation process described herein) to prevent such chemical reactions in order to maintain the nature of the active phase as close as possible compared to that was obtained on chemically inert macroscopic supports such as SiC or carbon. Accordingly, advantageously, the method of the invention further comprises a thermal treatment of heating the macroscopic composite obtained in step (f) (or obtained in step (e) if no step (f) is carried out) to a temperature ranging between 700–1000° C.±20° C. under inert atmosphere, preferably 600 to 900° C.±10° C., preferably 700 to 800° C., most preferably 700 to 900° C.±10° C. (step (g)). This step may be carried under nitrogen gas, or preferably under argon or helium gas. This step allows to improve the electrical and/or thermal conductivity of the final macroscopic composite (i.e., the end catalyst). This step also allows the complete conversion of some nitrogen species with lower stability into a more graphitized ones, i.e. pyridinic and quaternary species.

Advantageously, the thermal treatment step (g) may be carried out for several hours: from 1 hour to 10 hours preferably 2 hours. The total duration of this treatment depends also on the heating rate of the macroscopic support to the target treatment temperature and also on the total weight of the macroscopic composite to be treated. For example, the heating rate may be set-up between 0.5 to 20° C./min, preferably 2 to 10° C./min from the starting temperature (the temperature used in the preceding step of the method of the invention) to the target treatment temperature.

The heating ramp rate between the starting temperature and the target treatment temperature may be a linear one (a single linear heating slope, for example 10° C./min from the starting temperature to the target treatment temperature).

Alternatively, the overall heating ramp rate between the starting temperature and the target treatment temperature may comprise at least two successive linear heating up-ramps of different slopes. Preferably, the last heating up-ramp has a smaller slope than the preceding ones (slow heating in the last heating up-ramp stage to the target treatment temperature).

Advantageously, the overall heating ramp rate between the starting temperature and the target treatment temperature may comprise two successive linear heating up-ramps of different slopes. Preferably, the first heating up-ramp has a greater slope than the second (heating from the starting temperature to an intermediate temperature (for example 300-400° C.) for example at 2° C./min). Then, the second heating up-ramp from the intermediate temperature to the target treatment temperature may have a faster slope, for example up-ramp of 10° C./min from intermediate temperature 300° C. to target temperature 700° C.).

Advantageously, in the aqueous solution of step (a), $(NH_4)_2CO_3$ may be present at a concentration ranging from 1 to 8 mol/L preferably from 2 to 5 mol/L. The N-doping % and the porosity of the final macroscopic composite may be tuned within the depth of the carbonaceous layer by modulating the concentration of $(NH_4)_2CO_3$ or any other raw materials in the aqueous solution. For example, one can perform the process from step (a) to (f) followed by a second impregnation process with a solution having a lower concentration of $(NH_4)_2CO_3$. Such process can be repeated several times until the desired value is attained. The macroscopic composite (or catalyst) may be further graphitized at high temperature (step (g)).

Advantageously, in the aqueous solution of step (a), the carbohydrate carbon source may be present at a concentration ranging from 1 to 5 mol/L, preferably 2 to 4 mol/L. The porosity of the N-doped carbonaceous layer that coats the macroscopic support may be tuned by modulating the (ammonium carbonate and carboxylic acid)/carbohydrate molar ratio between each impregnation process [steps (a) to (f), or steps (a) through (e) when step (f) is omitted in favor of step (g)]. For example, the macroscopic support could be impregnated in a first iteration of the process (steps (a) to (f)) with an aqueous solution containing the different components with the following concentration: $(NH_4)_2CO_3$=1.2 mol/L, carbohydrate carbon=1.1 mol/L, citric acid=1.6 mol/L. The second impregnation process may be conducted with the same aqueous solution as before but with a higher $(NH_4)_2CO_3$ concentration of 3.8 mol/L. The higher $(NH_4)_2CO_3$ concentration will result into N@C layers featured by a higher porosity compared to that of the N@C layers obtained with lower $(NH_4)_2CO_3$ concentration of the first iteration process. The same process can be repeated until the total amount of N@C reaches the one defined for the macroscopic composite or catalyst (i.e., the target N-doping % in the macroscopic composite/catalyst). The final macroscopic composite may then be generated by submitting the composite to the last thermal treatment noted (g) at 700-1000° C.±20° C. under inert atmosphere, preferably 600 to 900° C.±10° C., most preferably 700 to 800° C.±10° C.

Advantageously, in the aqueous solution of step (a), the carboxylic acid source (for example citric acid) may be present at a concentration ranging from 1 to 3 mol/L, preferably 2 mol/L.

Advantageously, the immerging/soaking step (c) may be carried out for 1 to 10 minutes preferably 2 minutes. This is a stark advantage compared to methods known in the art. The method according to the invention needs only a very short contact time or wetting time between the macroscopic support and the aqueous solution of step (a). A similar time is needed when the macroscopic support is impregnated (when step (c) is an impregnating process, whether it be excess solvent impregnation or a pore-volume impregnation), and is only dependent on the size and weight of the support to be impregnated and the amount of the solution containing the active phase precursors.

Advantageously, the first thermal treatment step (e) may be carried out for several hours: from 1 hour to 10 hours, preferably 1 to 2 hours at the desired treatment temperature.

Advantageously, the second thermal treatment step (f) may be carried out for several hours: from 1 hour to 10 hours, preferably from 1 to 2 hours when the temperature used in step (f) is 400-500° C.±10° C., preferably 450° C.±5° C., most preferably 400° C.±5° C.; or 2 to 4 hours when the temperature used in step (f) is 300° C.±10° C. The total duration of this treatment depends also of the heating rate of the solid from room-temperature to the treatment temperature and also to the total weight of the macroscopic composite to be treated. For example, the heating rate may be set-up between 0.2 to 10° C./min, preferably 0.5 to 2° C./min, preferably 2° C./min.

In another aspect, the present invention provides a macroscopic composite coated with a layer of highly and tunable concentration N-doped mesoporous carbonaceous material obtainable by a method according to the present invention, including all the variants described herein.

In another aspect, the present invention provides a macroscopic composite coated with a layer of highly N-doped mesoporous carbonaceous material, wherein the N-doped carbonaceous material layer:
 has an N atom contents of 1-40%, preferably 5-40%, preferably 10-35%, preferably about 15% (e.g., 12-18%);
 has an average pore size of 2-50 nm, preferably 2-30 nm; most preferably 3-12 nm; and/or
 has a thickness of 5 to 200±5 nm, preferably 10 to 100±5 nm.

Advantageously, the macroscopic composite coated with a layer of highly N-doped mesoporous carbonaceous material according to the invention has an N atom % of 15-35%, preferably about 15% (e.g., 12-18%).

One of the stark advantages of the inventive method is that a liquid phase (e.g., aqueous solution of step (a)) is used to impregnate the macroscopic support, to lead to the formation of a highly N-doped carbonaceous layer on the support surface. This distinguishes from existing processes which use a solid phase or gas phase processes.

In another aspect, the present invention provides the use of the macroscopic composite coated with a layer of highly N-doped mesoporous carbonaceous material according to the invention as catalytic materials. One advantage of using macroscopic supports is directly linked with the reduction of pressure drop across the catalyst bed and also for an easy handling and transport of the catalyst. The macroscopic supports can be selected between those described above including grains, pellets, foams, etc, depending to the downstream applications. As discussed above, the presence of nitrogen atoms at the surface of the macroscopic composite materials, the nitrogen atoms being embedded in the porous carbon matrix coating, provides enhanced reactivity and also stability to the final composite. As such, the resulting coated material presents advantageous properties in terms of catalytic activity in various chemical reactions and catalytic transformations.

For example, the macroscopic composite coated with a layer of highly N-doped mesoporous carbonaceous material obtainable by a method according to the present invention may be used in several industrially relevant catalytic transformations such as the oxygen reduction reaction, the steam-free dehydrogenation of hydrocarbons (including aromatic hydrocarbons) or the partial oxidation of $H_2S$ into elemental sulfur, just to mention a few. The macroscopic composite (macroscopic support covered with a layer of nitrogen-doped mesoporous carbon) could also be used as catalytic support for metals or oxides in other relevant catalytic applications, such as the liquid-phase and gas-phase hydrogenation, the oxidation of linear alkanes and volatile organic compounds (VOCs), the hydrogenation of CO in the Fischer-Tropsch process, and methanization of synthesis gas mixture, just to mention a few.

In yet another example, the macroscopic composite coated with a layer of highly N-doped mesoporous carbonaceous material obtainable by a method according to the present invention may be used as metal-free catalyst in the Advanced Oxidation Processes for water and wastewater treatment. In this case, the N-doped carbonaceous layer may function as a solid matrix to fix carbon supports, such as carbon nanotubes, on the surface of a macroscopic support. As used herein, the expression "Advanced Oxidation Processes" (abbreviation: AOPs), in a broad sense, refers to a set of chemical treatment procedures designed to remove organic (and oxidizable inorganic) materials in water and waste water by oxidation through reactions with hydroxyl radicals (.OH). Typically, AOPs encompass (i) chemical oxidation processes using hydrogen peroxide, ozone, combined ozone & peroxide, hypochlorite, Fenton's reagent etc., (ii) ultra-violet enhanced oxidation such as UV/ozone, UV/hydrogen peroxide, UV/air; and (iii) wet air oxidation and catalytic wet air oxidation (where air is used as the oxidant). Advantageously, the macroscopic composite coated with a layer of highly N-doped mesoporous carbonaceous material obtainable by a method according to the present invention (N@C coated composites) may be used as metal-free catalyst in the catalytic ozonation of organic micropollutants (COZ) and/or the catalytic wet air oxidation (CWAO).

In another aspect, the present invention provides the use of the macroscopic composite coated with a layer of highly N-doped mesoporous carbonaceous material according to the invention for the manufacture of metal-free surface heater in inductive heating devices.

In another aspect, the present invention provides the use of the macroscopic composite coated with a layer of highly N-doped mesoporous carbonaceous material according to the invention as adsorbent for volatil organic compounds.

In another aspect, the present invention provides the use of the method according to the invention for the intimate assembling of two materials together, much like a solid glue. For example, the method of the invention may be used to glue together N-doped carbon nanotubes (which may be prepared by any method know in the art) and a macroscopic support, as described herein, in an effort to enhance the mechanical resistance of the assembly, which allows one to maintain a high and stable catalytic activity. The glue would be made up of the N-doped porous carbonaceous material that is formed in the course of carrying out the present method. Because of its high N-content, such glue would be less likely to dilute the active N-sites that are desirable and useful for a given catalytic reaction. The same coating method could also used to deposit the N-doped porous carbonaceous material onto hierarchical composites constituted by a macroscopic support decorated with nanoscopic carbon materials such as carbon nanotubes and nanofibers. The N-doped porous carbonaceous material layer will confer to the final composite a better mechanical strength for preventing matter lost during operation while the carbon nanotubes and nanofibers will provide high effective surface area for the composite.

As the reader will appreciate, the present invention provides multiple advantages:

The use of starting materials that are readily available, cheap, non toxic and environmentally friendly compounds such as ammonium carbonate (leavening agent), glucose/dextrose, maltose, lactose, and citric acid.

The possibility of depositing a homogenous active phase (highly N-doped mesoporous carbonaceous material) which, depending on the porosity of the active phase, could present an advantageous accessible surface provided the thickness is sufficient.

The possibility of depositing a thin film, with high accessibility, of the above mentioned active phase (highly N-doped mesoporous carbonaceous material) onto different macroscopic supports which are well adapted for catalytic processes by preventing a large pressure drop across the catalyst bed along with their easy handling and processability.

The macroscopic supports can be selected among those already available on the market such as alumina, silica and silicon carbide, and also other supports such as carbon, e.g. nanotubes or nanofibers, or activated charcoal, and the combination of the previously cited supports, either pure or doped with foreign elements.

The macroscopic supports used are produced industrially and thus, no further need for the support scale up is necessary to reduce the present invention to practice on an industrial scale (i.e., the invention is readily amenable/applicable for industrial scale applications).

The macroscopic composites of the present invention prove very useful as metal-free catalyst for oxygen reduction reaction (ORR). Thus, they are advantageous in terms of replacement of the expensive and scarce platinum catalyst (or platinum group metal catalyst, including noble metal alloys) that is conventionally used for that purpose. This constitutes one of the chief advantages of the method of the present invention.

The macroscopic composites of the present invention also prove very useful as catalyst for partial oxidation of gaseous $H_2S$ with large concentration range into elemental sufur. Thus, they are advantageous in terms of improvement of catalytic performance for the desulfurization of gaseous effluent in that reaction. The $H_2S$ concentration is relatively large and ranged between 0.1 to 15%, preferably 0.5 to 10% and especially 0.5 to 5%.

The macroscopic composites of the present invention prove very useful as catalyst for the selective gas-phase steam-free dehydrogenation of ethylbenzene into styrene. Thus, they are advantageous in terms of reducing the extra energy that is generally required to generate steam in that particular reaction.

The macroscopic composites of the present invention could also be used as catalyst support for metals and oxides active phase which can be used in other relevant catalytic processes, such as the liquid-phase and gas-phase hydrogenation, the oxidation of linear alkanes and volatil organic compounds (VOCs), the hydrogenation of CO in the Fischer-Tropsch process, and methanization of synthesis gas mixture, just to mention a few.

The macroscopic composites of the present invention can also be successfully used in a number of relevant catalytic transformations at the heart of renewable technologies, as they proved to be very useful as metal-free catalyst for Advanced Oxidation Processes for water and wastewater treatment, such as the catalytic ozonation of organic micropollutants (COZ) and/or the catalytic wet air oxidation (CWAO).

In the case where silicon carbide or carbon are used as supports the medium thermal conductivity of the silicon carbide and carbon will help in keeping the reaction temperature as stable as possible within the catalyst bed either in an exothermic (heat evacuation) or endothermic (heat retention) processes, notably thanks to the lack of resistance contact point between the macroscopic host support and the N-doped porous carbonaceous material. Notably, the above-mentioned interfacial resistance contact point is better than that observed in the catalytic bed, because the contact points between the composite support units (grains) cannot be overlooked.

The support of the spent catalyst (or macroscopic composite) could also be recovered by simply burning-out the N@C layer in air followed by new impregnation/drying/thermal step(s) (c) to (f) (or (c) to (g)) starting from a freshly prepared mixture (a) of the pre-catalytic aqueous phase. Such process is of extreme importance as it allows one to reduce the quantity of solid waste disposal as generally encountered with the commonly employed metal or metal-oxide based catalysts.

BRIEF DESCRIPTION OF THE DRAWINGS

Hereafter, the macroscopic composite or catalyst code is indicated as follows: $(G)N@C/SiC_g^{2nd}$, where (G) indicates that the catalyst has been graphitized under inert atmosphere at high temperature (700-1000° C.) (step (g)); N@C designates the nitrogen doped mesoporous carbon active phase; SiC refers to the nature of the support, e.g., silicon carbide (SiC), alumina ($Al_2O_3$), silica ($SiO_2$), etc.; subscript characters designates the macroscopic morphology of the support: (g) for grains, (e) for extrudates, (p) for pellets, (f) for foam; and the last superscript number designates the number of impregnation cycles followed by thermal treatment in air at 450° C. before the graphitization step (step (g)).

DETAILED DESCRIPTION

Equivalents

Figure 1:
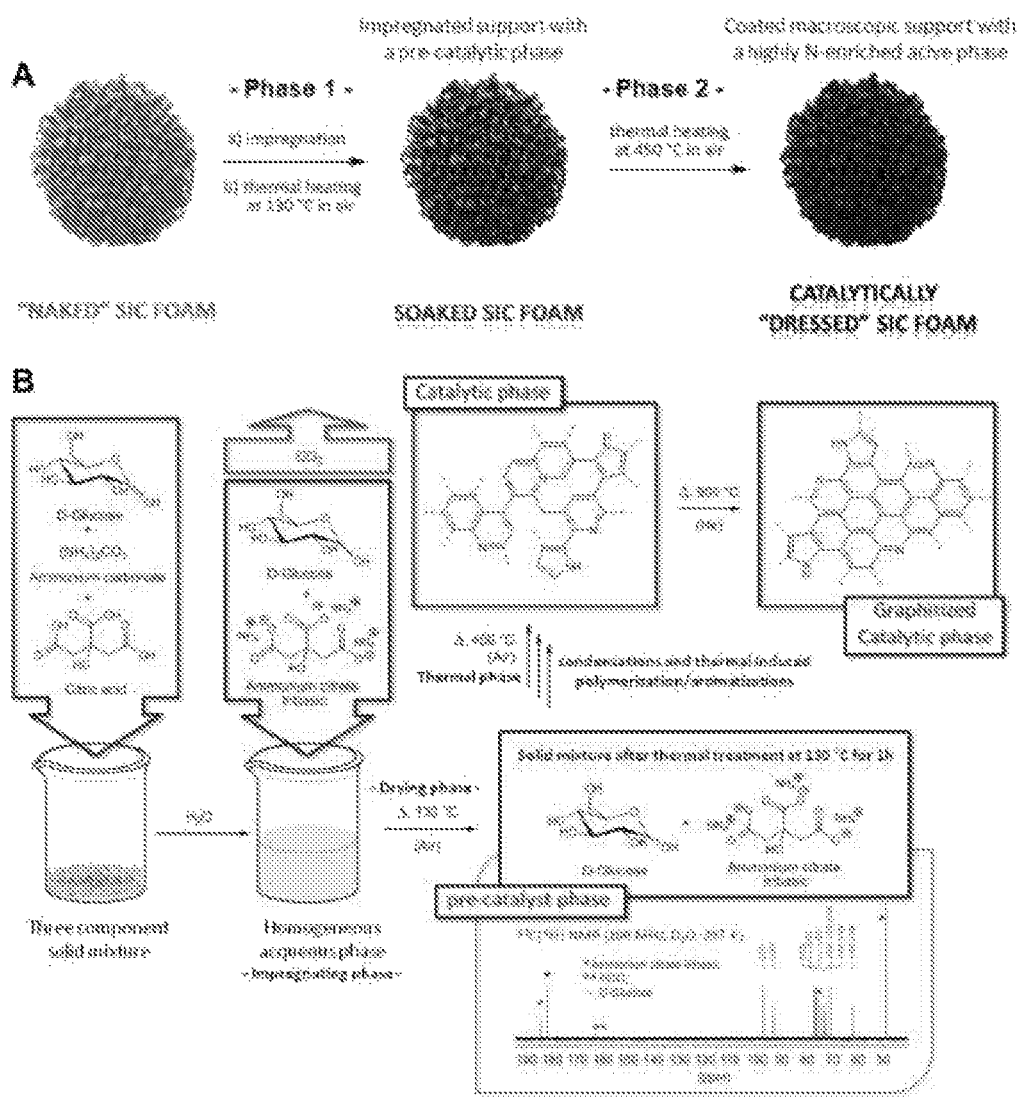
FIG. 1 schematizes an exemplary synthetic procedure for the preparation of macroscopic N-rich carbonaceous composites the invention. (A) Representation of a typical thermal sequence for "dressing" a model silicon-carbide foam support (SiC) with a mesoporous, N-rich catalytically active phase (N@C). (B) Provides the supposed mechanism for the thermal transformation of α,β-D-glucopyranose and ammonium citrate tribasic (pre-catalyst phase) into a N-rich mesoporous-carbon graphene-like network (N@C—catalytically active phase).

The representative examples that follow are intended to help illustrate the invention, and are not intended to, nor should they be construed to, limit the scope of the invention. Indeed, various modifications of the invention and many further embodiments thereof, in addition to those shown and described herein, will become apparent to those with ordinary skill in the art from the full contents of this document, including the examples which follow and the references to the scientific and patent literature cited herein. It should further be appreciated that the contents of those cited references are incorporated herein by reference to help illustrate the state of the art.

The following examples contain important additional information, exemplification and guidance that can be adapted to the practice of this invention in its various embodiments and the equivalents thereof.

Exemplification

The method and composites of this invention and their preparation can be understood further by the examples that illustrate some of the processes by which these composites are prepared or used. It will be appreciated, however, that these examples do not limit the invention. Variations of the invention, now known or further developed, are considered to fall within the scope of the present invention as described herein and as hereinafter claimed.

Example 1. General Procedure for a Highly N-Enriched Active Phase

In a typical procedure, 2 g of dextrose and 3 g of citric acid were added in deionized water (10 mL) at room temperature (r.t.). Then, a fixed amount of ammonium carbonate (i.e. 1, 2 or 3 g) was added in a single portion in the mixture solution at r.t. and an instantaneous effervescence due to CO$_2$ evolution was observed. The suspension was stirred at r.t. till a clear solution was obtained, that was used as a source mixture for the obtainment of N-doped carbonaceous materials deposited on suitable supports (upon support soaking/impregnation). As for the latter, 2 g of different supports were used, i.e. SiC extrudates (30 m$^2$ g$^{-1}$; SICAT), SiC powder (25 m$^2$ g$^{-1}$; SICAT) SiC foams (30 m$^2$ g$^{-1}$; SICAT), and α-Al$_2$O$_3$ beads (6 m$^2$ g$^{-1}$; Sasol). The wet solids were slowly heated in air from room temperature to 130° C. (heating rate of 10° C. min$^{-1}$) and keep at this temperature for 1 h. The as obtained dry solids were further impregnated with the same three component solution for several times until the desired loading was achieved. The solids were calcinated in air at 450° C. (heating rate of 2° C. min$^{-1}$ from r.t. to 450° C.) for 2 h during which the macroscopic host support was coated with a highly N-rich mesoporous carbonaceous phase. N@C composites obtained through 1 single impregnation phase, followed by thermal treatment at 130° C. and carbonization in air at 450° C. are named as N@C/SiC$_e^{1st}$. N@C composites obtained through two successive impregnation phases, each of them followed by thermal treatment at 130° C. and a final carbonization phase in air at 450° C. are named as N@C/SiC$_e^{2nd}$. The as-prepared solids were further graphitized under inert atmosphere in helium at 900° C. (heating rate of 10° C. min$^{-1}$ from r.t. to 900° C.) for 2 h in order to increase their final graphitization degree. The latter composites are named as (G)N@C/SiC$_e^{1st}$ (one impregnation step) and (G)N@C/SiC$_e^{2nd}$ (two impregnation step), respectively.

Example 2. Materials Characterization 1D ($^1$H and $^{13}$C{$^1$H}) NMR spectra of all samples were obtained on a Bruker Avance DRX-400 spectrometer (400.13 and 100.61 MHz for $^1$H and $^{13}$C, respectively). Chemical shifts (δ) are reported in ppm relative to trimethylsilane (TMS), referenced to the chemical shifts of residual solvent resonances ($^1$H and $^{13}$C).

Thermal gravimetry analysis (TGA) was performed on a Setaram apparatus with an air flow rate of 25 mL·min$^{-1}$ and a heating rate of 10° C.·min$^{-1}$ from room temperature to 1000° C. The specific surface area of the different samples was measured by the BET method using N$_2$ as adsorbent at liquid nitrogen temperature (TriStar sorptometer). Before measurement, the samples were outgassed at 200° C. overnight in order to desorb moisture and impurities on its surface. The XPS measurements of the support were performed on a MULTILAB 2000 (THERMO VG) spectrometer equipped with Al Kα anode (hv=1486.6 eV) with 10 min of acquisition. Peak deconvolution has been made with "Avantage" program from Thermoelectron Company. The C1s peak at 284.6 eV was used to correct charging effects. Shirley backgrounds were subtracted from the raw data to obtain the areas of the C1s peak. The gross morphology of the carbon and ceramic materials was observed by scanning electron microscopy (SEM) on a JEOL F-6700 FEG with an accelerating voltage of 10 kV. The transmission electron microscopy (TEM) measurements were performed by a JEOL 2100FX operating at 200 kV, equipped with GATAN Tridiem imaging filter and a prob-aberration corrector. The electron energy loss spectroscopy (EELS) analysis were performed in scanning mode (STEM) with 30 mrad convergent angle and 25 mrad collection angle. The spectral image was acquired in 20×33 pixels with exposure time of 1 s for each pixel. The energy resolution was 1.7 eV. Elemental signals were extracted from Si-L, C—K, N—K and O—K edges respectively. The Energy filtered TEM (EFTEM) measurements were made by three window method with energy slit of 8 eV, 30 eV and 20 eV and acquisition time of 10 s, 30 s and 40 s for Si, C and N respectively. The Raman analysis was carried out using a LabRAM ARAMIS confocal microscope spectrometer equipped with CCD detector. A laser line was used to excite sample, 532 nm/100 mW (YAG) with Laser Quantum MPC600 PSU. All the measurements were performed at room temperature. The Raman spectra were recorded using LabRAM ARAMIS Horiba Raman spectrometer equipment. Spectra were recorded over the range of 500-4000 $cm^{-1}$ at a laser excitation wavelength of 532 nm. The sample was deposited on a glass substrate by spin-coating its suspension and carefully dried before measurement.

Example 3. Catalytic Reactions 3.1 Oxygen Reduction Reaction (ORR).

Electrochemical studies were performed at 25° C. in a three-electrode cell in 0.1 M KOH supporting electrolyte, using Autolab PGSTAT30 (Eco Chemie, The Netherlands) potentiostat equipped with an analogue linear sweep generator at the sweep rate of 10 mV $s^{-1}$. Mercury oxide (Hg/HgO) electrode and Pt-wire electrodes were used as reference and counter electrodes, respectively. Unless otherwise stated, all potentials hereinafter are referred to the reversible hydrogen electrode (RHE). The electrochemical impedance spectroscopic (EIS) was used to determine the resistance of electrolyte solution.

10.0 mg of the catalyst sample, 5 mL isopropanol, and 50 μL Nafion solution (5 wt %) were ultrasonically mixed to form a homogenous catalyst ink. For the define RRDE test, the working electrode (PINE, AFE6R2GCPT) was prepared by loading 50 μL of catalyst ink onto a pretreated glassy carbon (GC) electrode (5.5 mm diameter and 0.2376 $cm^2$ geometrical area) and then dried at room temperature. The reference Pt data was recorded with a 20 wt % Pt/VXC-72 (Sigma) catalyst with a loading of 25 $\mu g_{pt}$ $cm^{-2}$.

All aqueous solutions were prepared using ultrapure water (18MΩcm, <3 ppb TOC) and supra-pure KOH (Sigma-Aldrich). In $O_2$-reduction experiments $O_2$ was constantly bubbled through the solution in order to maintain the saturation level and the ring potential was set at 1.2 V RHE in accordance with previous studies. Collection efficiency (N) was calculated from the experimental data obtained in 10 mM $K_3FeCN_6$ in 0.1M NaOH at standard measurement conditions (potential sweep rate 10 mV $s^{-1}$, 25° C.). The collection efficiency for the Pt(20%)/VXC-72 electrode was found to be 37%, This value was also reported by Wang (Yusheng Andrew Wang, B.A.Sc. The University of British Columbia, 2009) and Chlistunoff et al. (17)

The four-electron selectivity of catalysts was evaluated based on the $H_2O_2$ yield, calculated from the following equation:

$$H_2O_2(\%) = 200(J_R/N)/(J_R/N - J_D)$$

Here, $J_D$ and $J_R$ are the disk and ring currents density, respectively, and N is the ring collection efficiency.

The electron transfer number can be calculated in two ways. The first is to use the ring current and the disk current $n = -4J_D/(J_R/N - J_D)$. The second way to calculate n is by using the first-order Koutecky-Levich equation:

$$1/J_D = 1/j_k + 1/j_d$$

where $j_k$ is the kinetic current density and $j_d$ is the diffusion-limited current density through the expression $j_d = B\omega^{1/2} = 0.62 \, nF\gamma^{-1/6} D_{O_2}^{2/3} C_{O_2} \omega^{1/2}$. Here n is the average electron transfer number; F is the Faraday constant; γ is the kinematic viscosity of the electrolyte; $D_{O_2}$ is the oxygen diffusion coefficient (1.15×$10^{-5}$ $cm^2$/S); $C_{O_2}$ is the bulk oxygen concentration in the electrolyte (1.4×$10^{-6}$ mol/$cm^3$); and ω is the angular velocity of the electrode. The kinetic current density ($j_k$) and the Koutecky-Levich slope (1/B) can be obtained from a plot of 1/j versus 1/$\omega^{1/2}$.

3.2 Steam Free Dehydrogenation of Ethylbenzene.

The reaction was carried out in a fixed-bed continuous flow reactor under atmospheric pressure. The catalyst (300 mg) was loaded onto a quartz fritted disk located inside a tubular quartz reactor (id 8×length 800 mm). He gas was fed into the reactor at a flow rate of 30 mL·$min^{-1}$ through a mass flow controller (BROOKS MFC) and passed through a glass saturator filled with liquid EB maintained at 40° C. (EB partial pressure of 2922 Pa) using a thermal regulated bath.

The reaction system was heated to 550° C. and kept for 2 h under the He. The reactant flow (2.8 vol. % EB diluted in helium, total flow rate of 30 mL·$min^{-1}$) was then fed to the reactor. The reactant and the products (styrene (ST), benzene (BZ) and toluene (TOL) exit from the reactor was analyzed on-line with a PERICHROM (PR 2100) gas chromatography equipped with a flame detector (FID) and CP WAX S2CB column which was previously calibrated. In order to avoid any possible condensation of the reactant or the products all the tube lines were wrapped with a heating wire kept maintaining 110° C.

The ethylbenzene conversion ($X_{EB}$) and styrene selectivity ($S_{ST}$) were evaluated using equations: (2) and (3):

$$X_{EB} = \frac{F_0 C_{EB,inlet} - F C_{EB,outlet}}{F_0 C_{EB,inlet}} \times 100\% \quad (2)$$

$$S_{ST} = \frac{C_{ST,outlet}}{C_{ST,outlet} + C_{TOL,outlet} + C_{BZ,outlet}} \times 100\% \quad (3)$$

where F and $F_0$ are the flow rates of the outlet and inlet, respectively, and $C_{EB}$, $C_{ST}$, $C_{TOL}$ and $C_{BZ}$ represent the concentration of ethylbenzene, styrene, toluene and benzene. The carbon balances amounted to >96% in all investigations. The results were obtained after more than 30 h on stream with stable catalytic performance at testing conditions.

3.3 Partial Oxidation of $H_2S$ into Elemental Sulfur

The catalytic selective oxidation of $H_2S$ by oxygen (Eq. (1)) was carried out in an all glass tubular reactor working isothermally at atmospheric pressure.

$$H_2S + 1/2 O_2 \rightarrow 1/n\ S_n + H_2O\ \Delta H = -222\ kJ/mol \quad (1)$$

An amount of catalyst (300 mg) was placed on silica wool in a tubular Pyrex reactor (i.d. 16 mm), which was then placed inside a vertical tubular electrical furnace. The temperature was controlled by a K-type thermocouple and a Minicor regulator. The gas mixture of the reactant feed including $H_2S$ (1 vol %), $O_2$ (2.5 vol %), $H_2O$ (30 vol %), and He (balance) was passed downward through the catalyst bed. The gases flow rates were monitored by Brooks 5850TR mass flow controllers linked to a control unit. The weight hourly space velocity (WHSV) was fixed at 0.6 $h^{-1}$ and the $O_2/H_2S$ molar ratios of 5.

The reaction was conducted in a continuous mode. The sulfur formed in the reaction was vaporized because of the high partial pressure of sulfur at these reaction temperatures, and it was condensed at the exit of the reactor in a trap maintained at room temperature. The analysis of the inlet and outlet gases was performed online using a Varian CP-3800 gas chromatograph (GC) equipped with a Chrompack CP-SilicaPLOT capillary column and a thermal catharometer detector (TCD), which allowed the detection of $O_2$, $H_2S$, $H_2O$, and $SO_2$.

Summary of the Results of Examples 1 to 3:

We described above a new methodology for the obtainment of highly N-doped mesoporous carbons starting from simple, non-toxic raw foodstuff building blocks such as ammonium carbonate, citric acid and D-glucose; this latter being the most abundant sugar unit in biomass and the major product of the acid hydrolysis of lignocellulosic biomass. It is worthy to note that D-glucose could also be replaced by other sugars in the invention. The adopted protocol for the generation of a N-containing active phase includes a fundamental homogeneous aqueous pre-catalytic phase that can be used as an impregnating agent for a virtually infinite variety of macroscopic supports to be soaked. The macroscopic supports can be tuned at will, i.e. grains, pellets, rings, beads or foams, depending on the downstream application. The controlled thermal treatment of the impregnated supports allows for the N-containing mesoporous active phase to grow up as a coating of an ultimate composite material featured by a remarkably high percentage of exposed N-active sites.

Various composites prepared from different macroscopic host matrices have successfully been scrutinized as metal-free catalysts in three industrially relevant catalytic processes each of them with outstanding outcomes respect to either related metal-free or metal-based catalysts of the state-of-the-art. In particular, the electrochemical oxygen reduction reaction (ORR) (1), the super-Claus $H_2S$ oxidation into elemental sulfur for the purification of the gaseous effluents (4, 15) and the highly selective steam-free dehydrogenation of ethylbenzene into styrene (16) are discussed.

Figure 6:
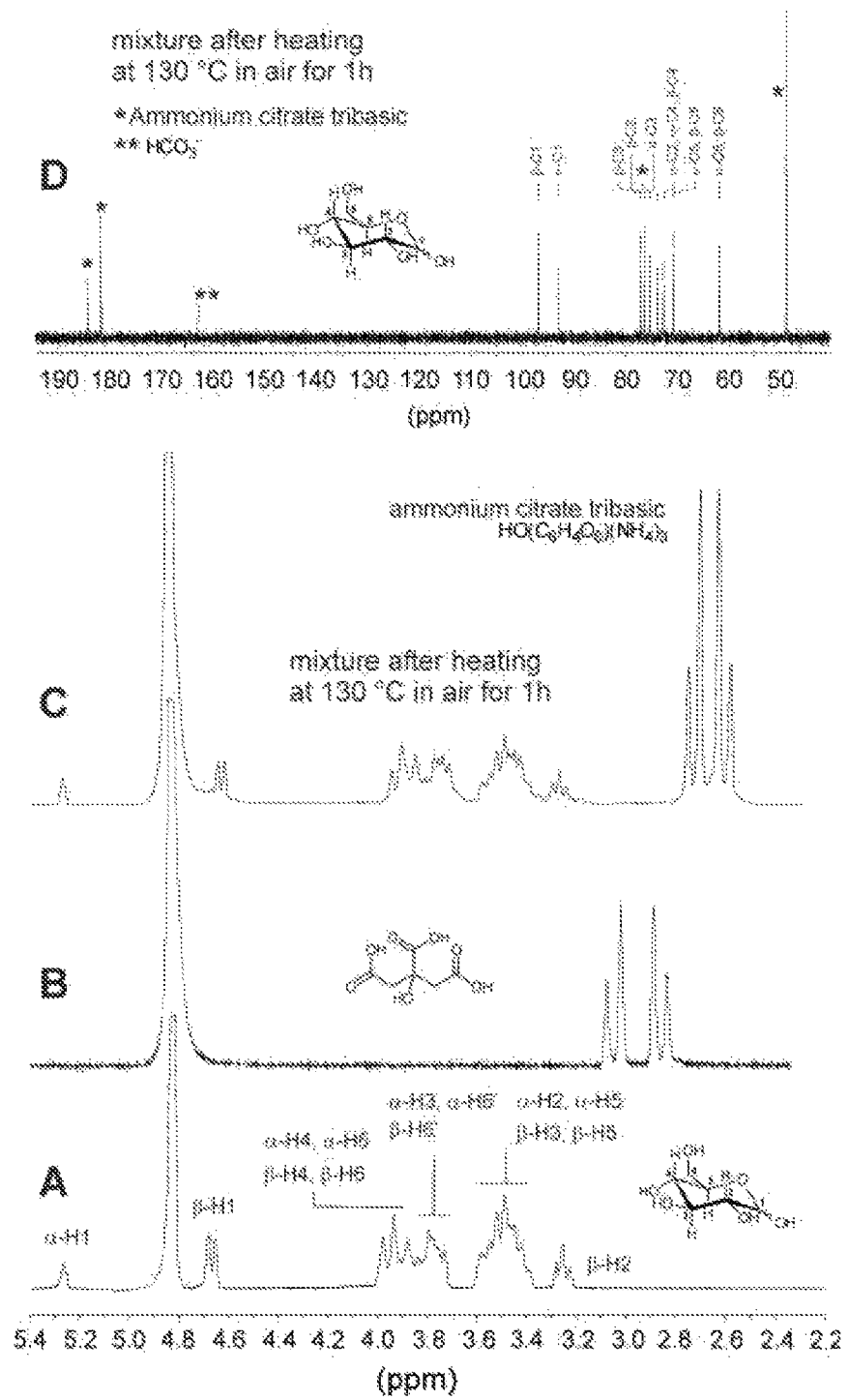
FIG. 6. $^1$H and $^{13}$C{$^1$H} NMR spectra (D$_2$O, 298 K) of a model three component mixture obtained by mixing 2 g of glucose, 2.3 g of ammonium carbonate and 3 g of citric acid, after heating at 130° C. for 1 h (C, D) and $^1$H and NMR spectra (D$_2$O, 298 K) of the two separate components, D-Glucose (A) and citric acid (B). From a close inspection of the $^1$H and $^{13}$C{$^1$H} NMR spectra in D$_2$O, the first thermal treatment at 130° C. of the three-component aqueous solution results into an homogeneous solid mixture of α-D-glucopyranose and β-D-glucopyranose and ammonium citrate tribasic. Almost no traces of either CO$_3^{2-}$ or HCO$_3^-$ are observed after this phase (D). Higher temperatures (450° C.) foster the progressive construction of a highly N-rich heteroaromatic network where the tribasic ammonium citrate simultaneously acts as N-reservoir (NH$_3$) and pores forming agent through its complete thermal decomposition in CO$_2$, H$_2$O and propene (Scheme 1).

The N-doped porous carbons, as a catalytic surface coating for different macroscopic host matrixes, were prepared by the impregnation of selected supports (i.e. powders, extrudates and silicon carbide (SiC) foams or $\alpha$-$Al_2O_3$ beads) with an homogeneous aqueous solution made of $(NH_4)_2CO_3$, glucose and citric acid, followed by two successive thermal treatments in air; the first one at moderate-temperature (130° C.) where the impregnating solution is slowly dried on the support thus forming a tiny pre-catalytic layer, and the second one at 450° C. (FIG. 6) where a support coating made of highly N-enriched active phase is generated (FIG. 1). The sample was further submitted to a graphitization process under inert gas at 800-900° C., in order to improve the electrical and thermal conductivity of the ultimate catalytic material and also to convert the nitrogen species into more stable and suitable forms for promoting the catalytic process. Depending to the downstream applications the last step is not always necessary.

D-Glucose and ammonium carbonate constitute the carbon and nitrogen sources, respectively, while the citric acid plays a double role as N-reservoir [in the form of mono-, di- and tri-basic ammonium citrate] and pores forming agent during the higher temperature thermal treatment (FIG. 1, 4 and Scheme 1).

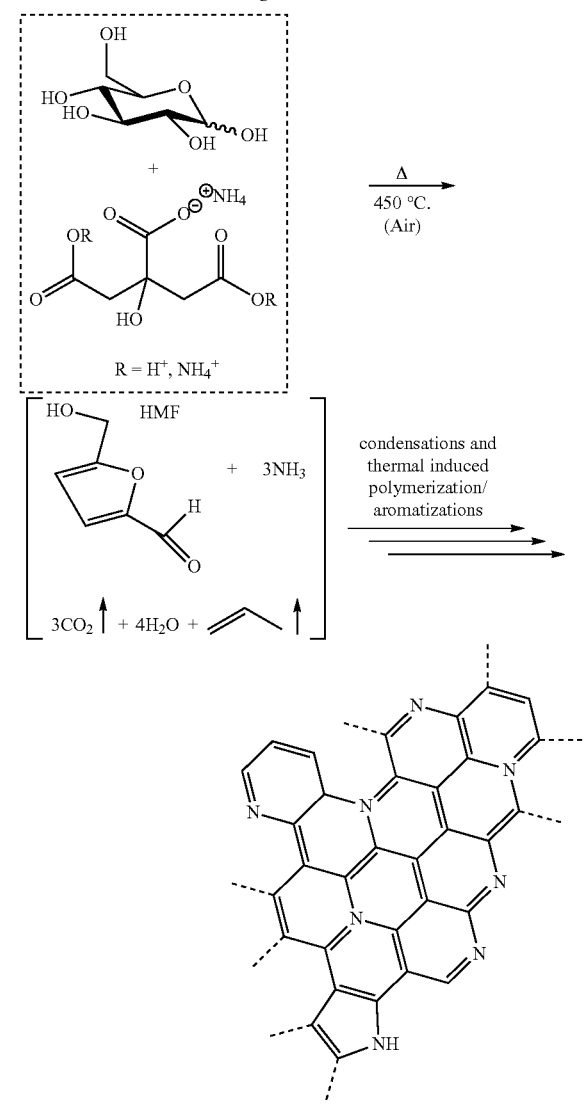

Without wishing to be bound by any particular theory, Scheme 1 presents a suposed mechanism for the thermal transformation of $\alpha,\beta$-D-glucopyranose and ammonium citrate tribasic (pre-catalyst phase) into a N-rich heteroaromatic graphene-like network (catalytically active phase).

The thermal treatment at 450° C. is supposed to start the progressive dehydration of the hexose sugar to give the 5-hydroxymethyl-furfural (5-HMF)(18) this latter being one of the most attractive chemical platforms for the synthesis of more complex chemicals and materials.(20) Although, further insights are required to ascertain the exact nature of the reactions occurring under these thermal conditions, ammonium citrate tribasic, is expected to act as a reservoir of nucleophilic $NH_3$ that is promptly trapped (20) in the polymerization procedure thus leading to nitrogenated compounds (21-23). The fate of the citric acid core is that of its complete decomposition to the elemental volatiles $CO_2$, $H_2O$ and propene which reasonably contribute to the ultimate material mesoporosity.

Figure 7:
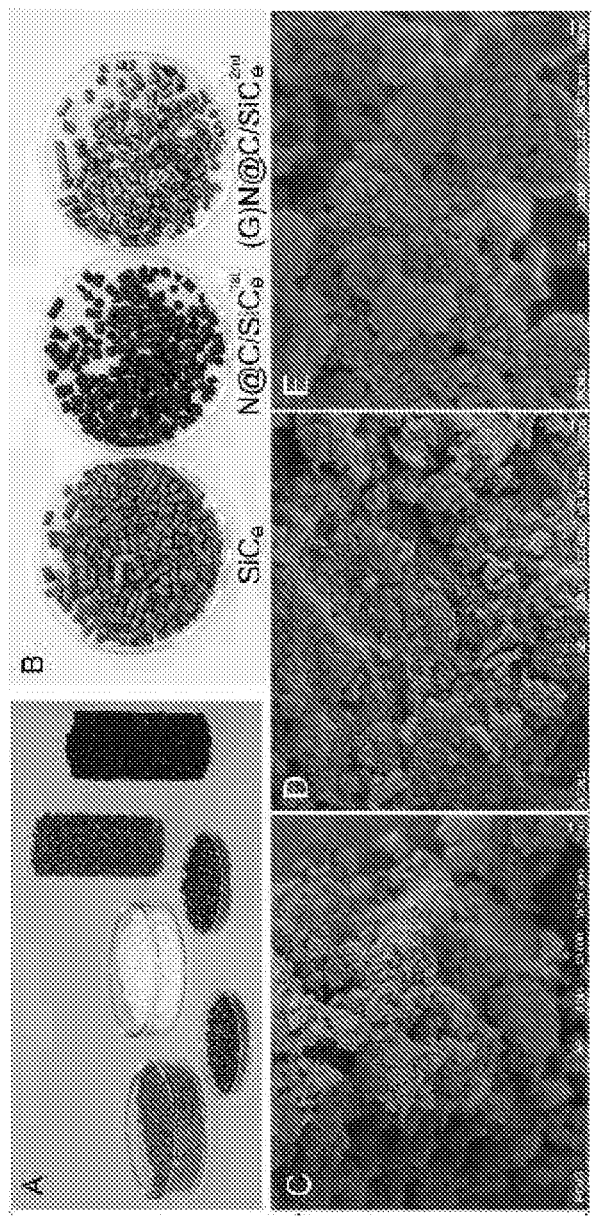
FIG. 7. (A) Digital photo of different macroscopic materials as supports (host matrices) for the N@C active phase. (B) Digital photos of the pristine SiC, and the N@C decorated macroscopic host structures after thermal treatment in air and graphitization under helium at 900° C. (C-E) SEM images of the (G)N@C/SiC$_e^{2nd}$ composite showing typically micro- and meso-porous structured surfaces.
Figure 8:
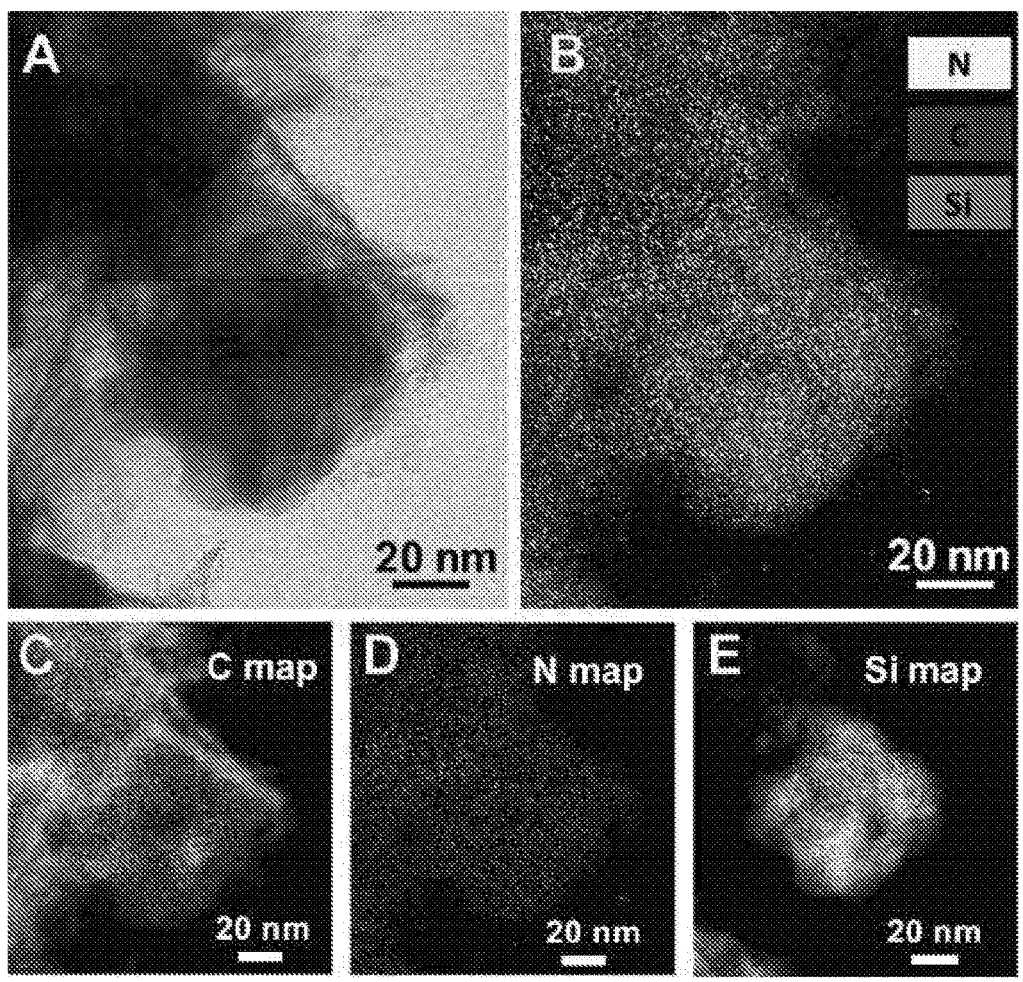
FIG. 8. TEM and EFTEM mapping of a (G)N@C/SiC$_e^{2nd}$ sample (Table 1, entry 5). (A) TEM bright-field image. (B) Elemental maps, the fack colors correspond to Nitrogen, Carbon and Silicon. (C) Carbon map (D) Nitrogen map (E) Silicon map.

The thickness of the N-doped carbonaceous coating on the macroscopic support can be improved by repeating the impregnation/drying step (FIG. 1, phase 1) before proceeding with the final high temperature thermal treatment of the composite to obtain the active phase (FIG. 1, phase 2 and FIG. 7).

Figure 2:
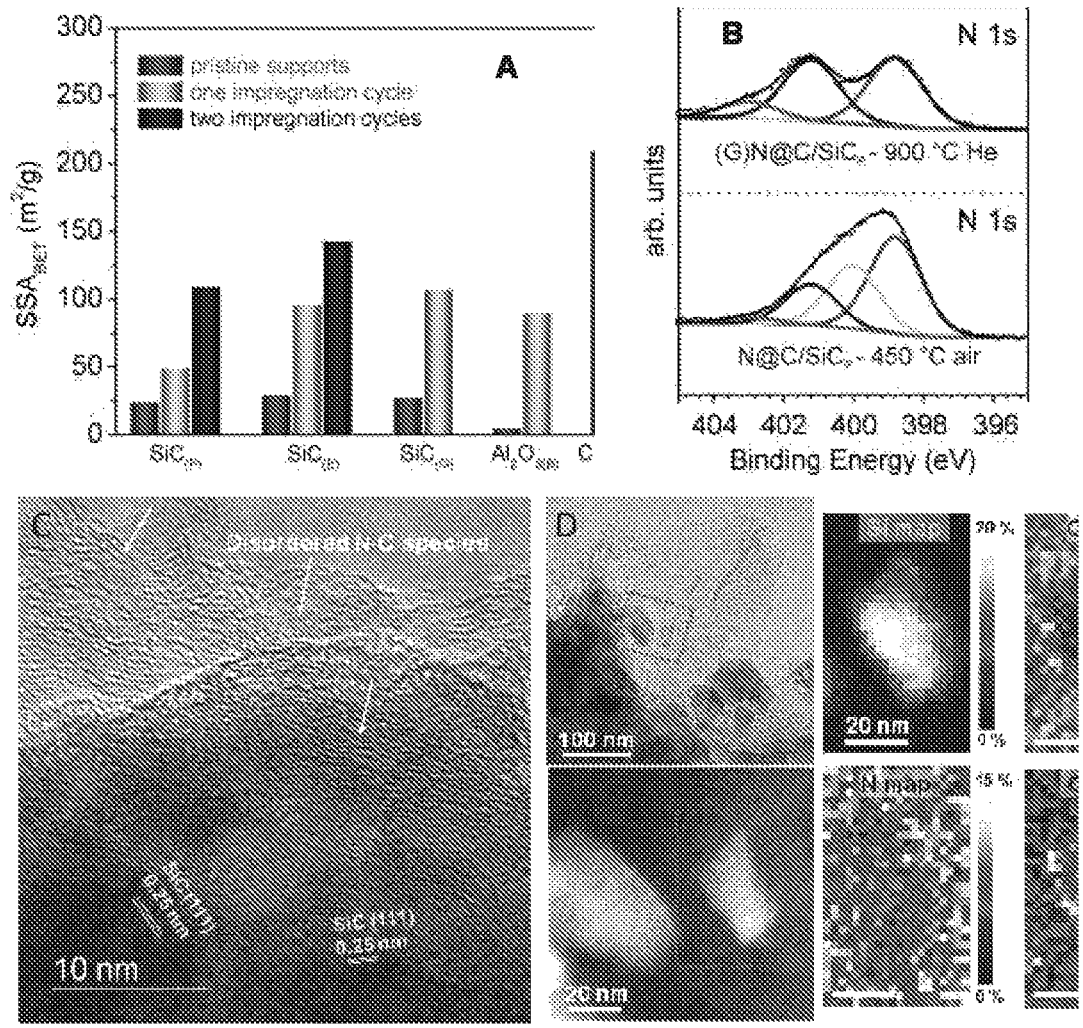
FIG. 2 reports selected chemico-physical and morphological characterizations of a $(G)N@C/X_g^{2nd}$ active phase prepared according to the method of the invention. (A) BET specific surface area of the as-prepared $(G)N@C/X_g^{2nd}$ (with X=SiC in the form of powder, grains, extrudates and $Al_2O_3$ in the form of beads) prepared on supports featured by different chemical composition, shape and size. (B) XPS N is spectra analysis of the nitrogen species present in the N@C catalytically active phase (Thermal treatment: 2 h at 450° C. in air (N@C/$SiC_p$) and then graphitized ((G)N@C/$SiC_p$) 2 h at 900° C. under helium atmosphere) (C) HRTEM micrographs of the N@C layer at the $(G)N@C/SiC_g^{2nd}$ composite [N-doped composite based on SiC grains as support, after 2 impregnation cycles (c-e steps), thermal treatment at 450° C. (f step) and graphitization at 900° C. under helium atmosphere (g step)]. (D) (Top left) An overview bright field TEM image. (Bottom left) A high-angle annular-dark-field image (STEM-HAADF) which was taken from the area marked by the dashed-line box on the top left image. (Four images on the right side) elemental maps of Silicon, Carbon, Nitrogen and Oxygen respectively taken from the area highlighted by the dashed-line box in the bottom-left image. The colors correspond to the relatively atomic composition ratio indicated by the adjacent vertical bars.
Figure 3:
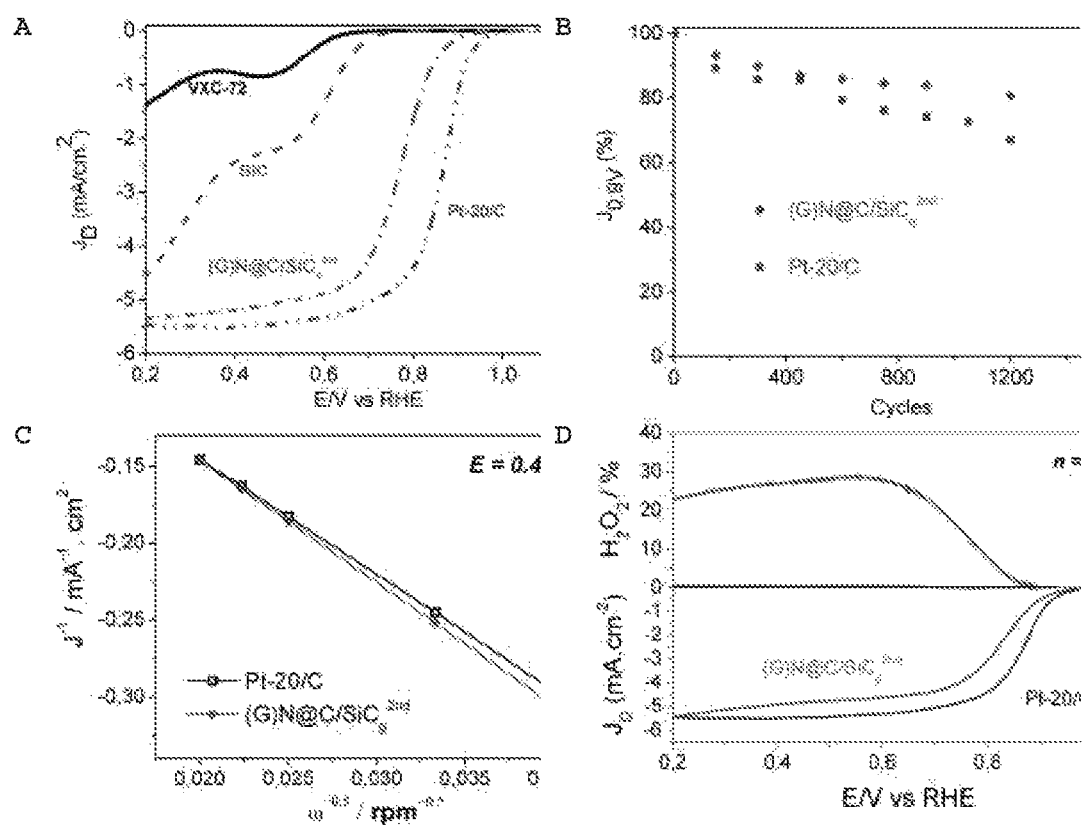
FIG. 3 illustrates an exemplary catalytic application of a $(G)N@C/SiC_g^{2nd}$ catalyst prepared according to the invention, in the electrocatalytic Oxygen Reduction Reaction. (A) ORR performance of the $(G)N@C/SiC_g^{2nd}$ (Average SiC size: 40 μm, 450 μg·cm$^2$ of N@C active phase), VXC-72 (100 μg·cm$^2$ of N@C active phase) and Pt-20/XC72 Vulcan (25 $\mu g p_{Pt} \cdot cm^{-2}$), reaction temperature=25° C., rpm=1600 rpm, KOH 0.1 M). (B) Long-term stability of the (G)N@C/$SiC_g^{2nd}$ and Pt-20/XC72 catalysts at 25° C. with a RRDE system. The test was carried out for 1,500 cycles between 1.0 and 0.6 mV. (C) Koutecky-Levich plots as recorded at 0.4V for curves registered at different electrode rotation rates (rpm) (D) RRDE measurements on both (G)N@C/$SiC_g^{2nd}$ and Pt-20/C catalysts under alkaline environment (KOH 0.1M at 25° C.) and respective ring current values ($H_2O_2$ production) for the calculation of the average number of electron transfer.

The host matrix coating based on a N-rich nanocarbon phase (N@C), prevalently featuring meso- and macroporosity, increases the specific surface area (SSA) of the final composite remarkably (FIG. 2A). Similarly to above, successive impregnation/drying cycles (FIG. 1, phase 1) were exploited to additionally increase the ultimate SSA of the catalytic composite. The high resolution N is XPS analysis of the composites show characteristic profiles featured by two main component at 399 and 401 eV, consisting in pyridinic and pyrrolic nitrogen species, respectively (FIG. 1B). The total nitrogen content spans in the 6%-28 at. % range and it can be controlled by tuning the ammonium carbonate/D-glucose/citric acid molar ratio as well as the number of impregnation cycles (Table 1). The high nitrogen loading and its almost exclusive localization on the topmost surface of the support in the present work is additionally Oxygen Reduction Reaction (ORR) experiments have been performed under alkaline environment (KOH 0.1 M), using the $(G)N@C/SiC_g^{2nd}$ catalyst (for detail see Table 1) as the most representative catalyst from this series, prepared from SiC powder as support (diameter ranged between 10 to 40 μm). FIG. 3A shows its remarkable electrochemical performance in a direct comparison with that of the commercially available Pt-20/C (Vulcan XC-72 with platinum loading of 20 wt %) and the pristine SiC powder support under identical conditions. The Koutecky-Levich (K-L) plots of the two catalysts show similar trends thus indicating a near four electrons mechanism operating at both systems (FIG. 3C). A more accurate estimation of the number of electrons transferred (n) per mol of $O_2$ (and the % of $H_2O_2$ produced by the catalysts in the electrochemical process) is calculated from the Pt-ring current values measured at the rotating-ring-disk electrode (RRDE) (FIG. 3D). The average values of n as calculated from both approaches are equal to 3.6 and 4 for the $(G)N@C/SiC_g^{2nd}$ and Pt-20/C catalysts, respectively. The onset potential ($E_{on}$) of CNT foam sample is close to that of the reference Pt-Vulcan sample (~1V) but the half potential still lower (around 60 mV less). The $E_{1/2}$ and the intensity at 0.9V show that the activity of the $(G)N@C/SiC_g^{2nd}$ is slightly less active than the Pt/C.

Cycling electrochemical tests in the 0.6-1.0 V range (at 100 mVs$^{-1}$, 900 rpm in 0.1 M KOH at 25° C.) have been used to check the $(G)N@C/SiC_g^{2nd}$ vs. Pt-20/C catalyst stability. Notably, the selected metal-free system retains about 90% of its initial ORR activity after 1500 cycles whereas only 70% is maintained by the Pt-20/C catalyst (FIG. 3B). Such a remarkable electrochemical stability (similarly reported for vertically-aligned N-doped carbon nanotubes by other research team (24, 24a, 24b), in combination with the catalysts performance in the ORR, makes these systems a valuable alternative to the existing precious metal-based catalysts.

TABLE 1

Preparation of N@C composites based on extrudates SiC (host matrix) and N-composition.[a]

| Entry | Impregn. cycles | 1$^{st}$ impregn. cycle (NH$_4$)$_2$CO$_3$ (g) | 2$^{nd}$ impregn. cycle (NH$_4$)$_2$CO$_3$ (g) | N at %[b] | Nitrogen species (at. %)[b] | | | |
|---|---|---|---|---|---|---|---|---|
| | | | | | Pyridinic | Pyrrolic | Graphitic | Oxidized |
| 1 | 1 | 0.75 | — | 7.33 | 0.32 | 3.86 | 2.82 | 0.33 |
| 2 | 1 | 2.3 | — | 9.68 | 0.29 | 5.31 | 3.57 | 0.51 |
| 3[c] | 1 | 2.3 | — | 6.93 | 2.35 | 2.49 | 1.41 | 0.68 |
| 4 | 2 | 2.3 | 0.75 | 13.40 | 6.28 | 4.08 | 2.64 | 0.40 |
| 5[c] | 2 | 2.3 | 0.75 | 8.11 | 0.52 | 0.32 | 2.89 | 0.74 |
| 6 | 2 | 2.3 | 1.5 | 28.45 | 13.05 | 7.86 | 5.59 | 1.95 |
| 7[c] | 2 | 2.3 | 1.5 | 11.80 | 4.59 | 1.24 | 4.47 | 1.50 |
| 8 | 2 | 2.3 | 2.3 | 28.59 | 12.74 | 8.07 | 5.64 | 2.14 |
| 9[c] | 2 | 2.3 | 2.3 | 12.84 | 5.22 | 1.44 | 4.56 | 1.62 |

[a]Materials and reaction conditions: SiC extrudates (2 g); D-glucose (2 g); Citric acid (3 g). Each sample undergoes a thermal treatment (drying) at 130° C. for 1 h in air after each impregnation cycle with an aqueous pre-catalytic phase made of D-glucose/citric acid and ammonium carbonate [from steps (c) to step (e)]. Each sample undergoes additional thermal treatment in air at 450° C. for 2 h [step (f)].
[b]The nitrogen content (at. %) in the finial N@C composites as measured by XPS analysis.
[c]The composite undergoes graphitization at 900° C. under inert atmosphere (He) for 2 h.

confirmed by high-resolution TEM and TEM-EELS analysis of the N-doped nanomaterial deposited on the SiC host matrix (FIG. 2C,D). These unique material properties makes these composites ideal single-phase, metal-free systems for promoting a high number of industrially relevant catalytic transformations with excellent or even better performance than that of the heterogeneous metal/metal-oxide based counterparts of the state-of-the-art.

Figure 4:
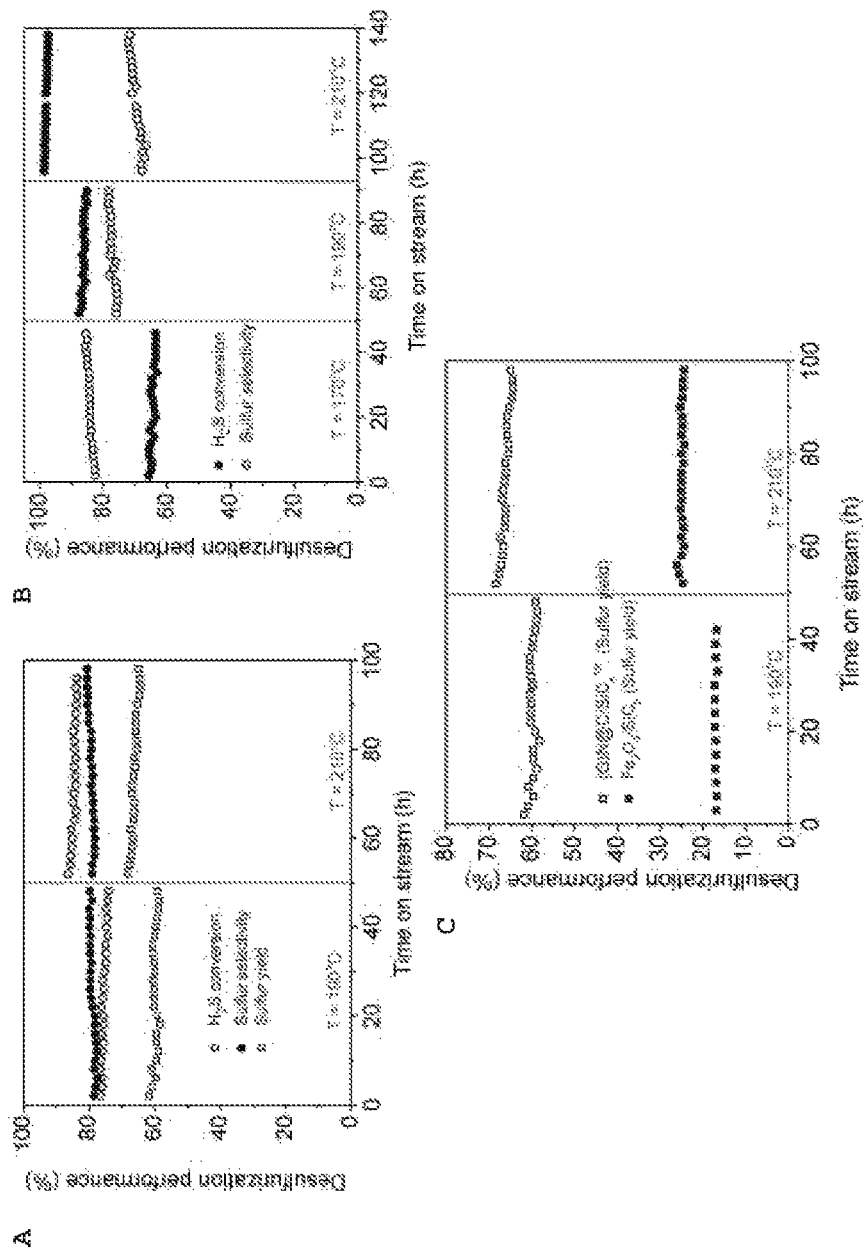
FIG. 4 illustrates an exemplary catalytic application of $(G)N@C/SiC_e^{1st}$-composites prepared according to the invention, in the high temperature, oxidation of $H_2S$ residues (desulfurization) from gaseous industrial effluents. (A) Desulfurization performance of the $(G)N@C/SiC_e^{1st}$ (Entry 3, Table 1) catalyst as a function of the reaction conditions ($m_{catalyst}$=1 g, $O_2$/$H_2S$ molar ratio=2.5, Weight Hourly Space Velocity (WHSV)=0.6 h$^{-1}$) (B) $H_2S$ conversion and sulfur selectivity by catalyst $(G)N@C/SiC_e^{1st}$ as function of the reaction temperature. (Reaction conditions: $m_{catalyst}$=1 g; Weight Hourly Space Velocity (WHSV)=0.6 h$^{-1}$; $O_2$/$H_2S$ molar ratio=2.5) (C) Direct comparison of desulfurization performance of catalysts $(G)N@C/SiC_e^{1st}$ and $Fe_2O_3$/SiC ($m_{catalyst}$=1 g, $O_2$/$H_2S$ molar ratio=2.5, Weight Hourly Space Velocity (WHSV)=0.6 h$^{-1}$).
Figure 5:
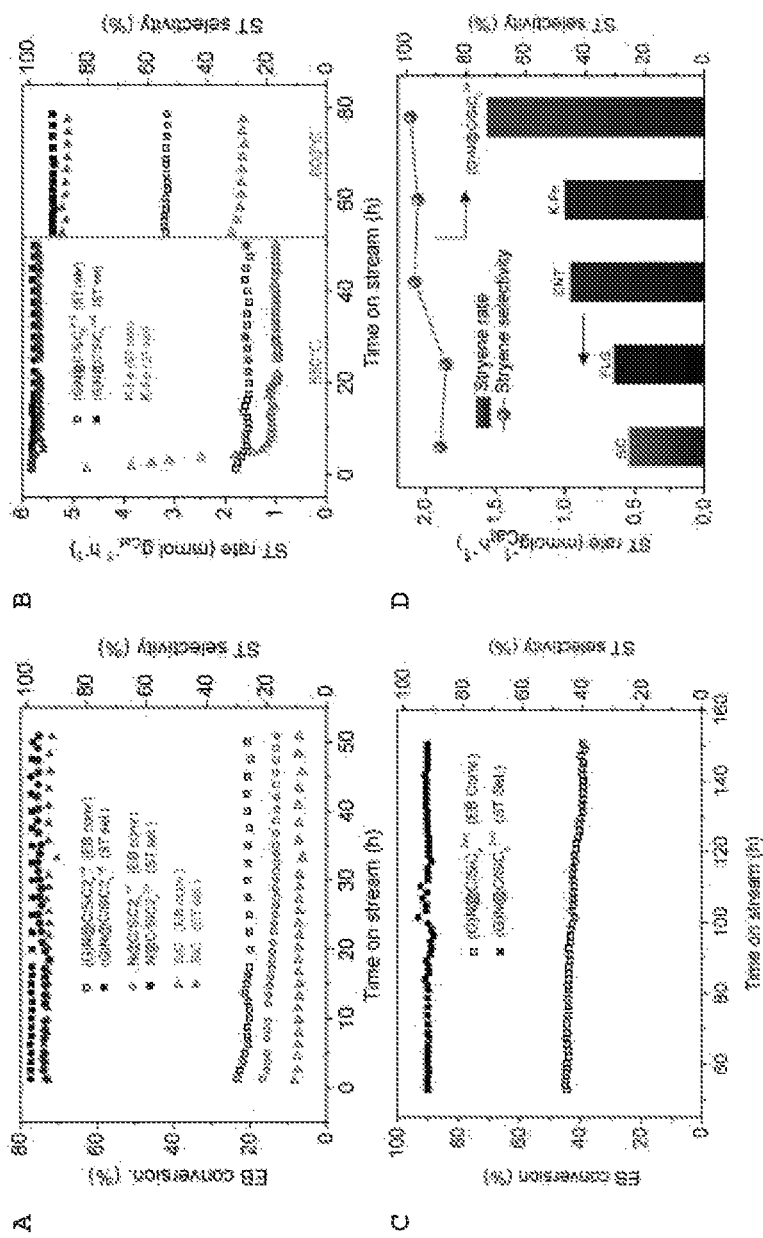
FIG. 5 illustrates an exemplary catalytic application of N@C-composites prepared according to the invention, in the steam-free direct dehydrogenation (DH) of ethylbenzene (EB) into styrene (ST). (A) Ethylbenzene dehydrogenation performance of the (G)N@C/SiC$_e^{2nd}$ catalyst (Entry 5, Table 1), its graphitized form (G)N@C/SiC$_e^{2nd}$ (Entry 5, Table 1) and the pristine support. (B) Catalytic performance of the industrial K—Fe-based catalyst and (G)N@C/SiC$_e^{2nd}$ at 550 and 600° C., respectively. (C) Long-term DH test at 600° C. with the (G)N@C/SiC$_e^{2nd}$ catalyst (reaction conditions: 300 mg, 600° C.). (D) Benchmarking of various carbon-based industrial catalysts and the (G)N@C/SiC$_e^{2nd}$ system under steady state (Reaction condition: 550° C. 2.8% EB in helium, 30 mL·min$^{-1}$, atmospheric pressure).

Table 1 reports different preparation parameters of a model $N@C/SiC_e$ and $(G)N@C/SiC_e$ composite according to the invention and the related nitrogen elemental composition. These composites are employed in the super-Claus $H_2S$ oxidation reaction as shown and detailed in FIG. 4. These composites are also employed for the material characterization and for the electrochemical Oxygen Reduction Reaction (ORR) (See FIG. 3 and related details). These composites are also employed in the steam-free direct dehydrogenation (DH) of ethylbenzene (EB) into styrene (ST) (See FIG. 5 and related details).

The (G)N@C/SiC$_e^{1st2nd}$ catalyst (for detail see Table 1) has also shown excellent catalytic performance under more severe reaction conditions, once employed for the partial oxidation of H$_2$S residues (desulfurization) in the gaseous industrial effluents, in agreement with the current legislation constraints. This metal-free system exhibits an relatively high desulfurization performance with a sulfur yield closed to 70% when the process is performed at 210° C. with a Weight Hourly Space Velocity (WHSV) of 0.3 h$^{-1}$ (FIG. 4A-C). For the sake of comparison, the desulfurization test has been also carried out using one of the most active and selective desulfurization system of the state-of-the-art like the Fe$_2$O$_3$/SiC$_p$ catalyst. This latter show a remarkably lower desulfurization activity compared to that of the (G)N@C/SiC$_e^{1st}$ catalyst (FIG. 4C) under similar reaction conditions. This latter catalyst also exhibits an extremely high stability as almost no deactivation is observed after hundred hours of reaction (FIG. 4A). XPS analysis carried out on the spent catalyst shows no evidence of nitrogen species modification (Table 2) and confirm the high stability of the catalyst under the selective oxidation reaction. Such a high stability can be attributed to the chemical inclusion of nitrogen atoms in the carbonaceous matrix which significantly prevent leaching effects of the active phase whereas active phase sintering effects are definitively ruled out thanks to the nature of the metal-free system used.

Figure 9:
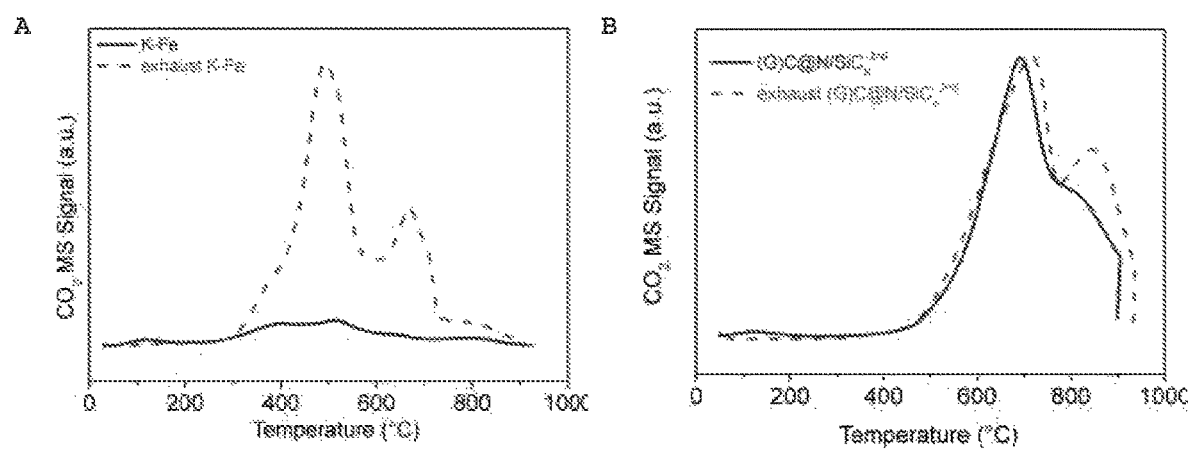
FIG. 9. TPO-MS analysis of (A) the industrial Fe—K/Al$_2$O$_3$ and the (G)N@C/SiC$_e^{2nd}$ (Entry 5, Table 1) catalysts before and after EB dehydrogenation test illustrating the coke resistance of the (G)N@C/SiC$_e^{2nd}$ system.

The (G)N@C/SiC$_e^{2nd}$ (for detail see Table 1) catalyst was also evaluated in the more drastic steam-free direct dehydrogenation of ethylbenzene (EB) into styrene in a fixed-bed configuration. The effluent was analyzed by online gas chromatography (GC). At 550° C., EB conversion was 22% (specific rate of 300 mmol/g$_{cat}$/h) and increased with increasing the reaction temperature to reach 44% at 600° C. (specific rate of 600 mmol/g$_{cat}$/h) (FIG. 5B). The catalyst selectivity towards styrene was almost 100% for the whole test at 550° C. while slight selectivity decrease was observed at higher reaction temperature (600° C.), where small amounts of toluene and benzene (<2%) are formed as reaction by-products. Under the same reaction conditions the Fe—K/Al$_2$O$_3$ (with 90 wt % of Fe loading) catalyst shows a much lower dehydrogenation activity (FIG. 5A,B). The Fe—K/Al$_2$O$_3$ catalyst shows a high DH activity at the beginning of the test followed by a sharp deactivation down to 5% of EB conversion (FIG. 5A,B). The metal-free catalyst exhibits an extremely high stability as almost no deactivation was observed for long term duration tests (FIG. 5C). The blank test carried out on the SiC extrudates shows a relatively low DH activity (FIG. 5A) and confirms the high DH activity of the SiC supported nitrogen-doped porous carbon. The deactivation observed on the Fe—K/Al$_2$O$_3$ catalyst was attributed to the progressive coverage of the iron-based catalyst by a layer of coke residues as shown by the temperature-programmed oxidation (TPO) analysis (FIG. 9). On the (G)N@C/SiC$_e^{2nd}$ catalyst the TPO spectrum only shows a small amount of carbonaceous residue which accounts for a higher stability and durability of the metal-free catalyst (FIG. 9). The specific reaction rate, expressed in terms of molecules of EB converted per gram of active phase per hour, obtained on the different catalysts is presented in FIG. 5A and confirms again the higher DH activity of the (G)N@C/SiC$_e^{2nd}$ catalyst (26, 27).

The high catalytic performance of the nitrogen-doped porous carbon studied in the present work could be attributed to the electronic modification of the carbon atoms by the adjacent nitrogen atoms according to the pioneer work by Gong et al. (1) The high activity of the nitrogen-doped catalyst in the ORR and H$_2$S oxidation could be attributed to the high ability of the doped carbon surface to adsorb oxygen in a dissociative way to produce highly reactive adsorbed oxygen species which will be incorporated in the final product before escaping.

The spent catalysts, i.e. (G)N@C/SiC$_g^{2nd}$ grains (<40 μm) for ORR, (G)N@C/SiC$_e^{2nd}$ extrudates (1×2 mm) for selective oxidation of H$_2$S and steam-free dehydrogenation of ethylbenzene, are further characterized by mean of the XPS, BET specific surface area measurements and TPO and the results confirm the complete retention of the catalyst characteristics similar to those obtained on the fresh ones. Such results indicate that nitrogen active sites or specific surface area lost are unlikely to occur and highlight again the extremely high stability of these nitrogen-doped mesoporous carbon active phase.

In summary, a high nitrogen-doped porous carbon can be prepared through a simple chemical reaction involving non-toxic raw materials such as ammonium carbonate, glucose and citric acid mixture at relatively low-temperatures. The method developed also allows one to prepare these nitrogen-carbon composites, not only in a powder form but also with controlled shapes along with high mechanical anchorage, for use as metal-free catalysts in specific gas-phase and liquid-phase processes. The conversion of the nitrogen and carbon sources is extremely high which is not the case of traditional synthetic routes where a large amount of precursors decomposes leading to the formation of high waste amount. Last but not least the overall cost linked with this synthesis process is expected to be much lower than those encountered with traditional nitrogen-doped composites where toxic (or explosive) and high price raw materials, high waste release and high temperature operating are encountered. It is expected that the nitrogen-doped porous carbon prepared in greener conditions than those reported up to date can open the way to the development of new catalytic metal-free platforms featured by higher robustness and low operating costs, in a variety of catalytic processes beyond those exemplified in Example 3, including but not limited to, the liquid-phase and gas-phase hydrogenation, the oxidation of linear alkanes and volatil organic compounds (VOCs), the hydrogenation of CO in the Fischer-Tropsch process, and methanization of synthesis gas mixture, as well as Advanced Oxidation Processes for water and wastewater treatment, such as the catalytic ozonation of organic micropollutants (COZ) and/or the catalytic wet air oxidation (CWAO).

While we have described a number of embodiments of this invention, it is apparent that our basic examples may be altered to provide other embodiments that utilize the catalysts and methods of this invention. Therefore, it will be appreciated that the scope of this invention is to be defined by the appended claims rather than by the specific embodiments that have been represented by way of example.

LIST OF REFERENCES

1. K. P. Gong, F. Du, Z. H. Xia, M. Durstock, L. M. Dai, Nitrogen-Doped Carbon Nanotube Arrays with High Electrocatalytic Activity for Oxygen Reduction. *Science* 323, 760-764 (2009).
2. Y. G. Li et al., An oxygen reduction electrocatalyst based on carbon nanotube-graphene complexes. *Nat Nanotechnol* 7, 394-400 (2012).
3. R. L. Liu, D. Q. Wu, X. L. Feng, K. Mullen, Nitrogen-Doped Ordered Mesoporous Graphitic Arrays with High Electrocatalytic Activity for Oxygen Reduction. *Angew Chem Int Edit* 49, 2565-2569 (2010).
4. K. Chizari et al., Nitrogen-Doped Carbon Nanotubes as a Highly Active Metal-Free Catalyst for Selective Oxidation. *Chemsuschem* 5, 102-108 (2012).
5. D. S. Su, S. Perathoner, G. Centi, Nanocarbons for the Development of Advanced Catalysts. *Chemical Reviews* 113, 5782-5816 (2013).
6. C. W. Zhou, J. Kong, E. Yenilmez, H. J. Dai, Modulated chemical doping of individual carbon nanotubes. *Science* 290, 1552-1555 (2000).
7. X. R. Wang et al., N-Doping of Graphene Through Electrothermal Reactions with Ammonia. *Science* 324, 768-771 (2009).
8. S. G. Zhang, M. S. Miran, A. Ikoma, K. Dokko, M. Watanabe, Protic Ionic Liquids and Salts as Versatile Carbon Precursors. *J Am Chem Soc* 136, 1690-1693 (2014).
9. X. H. Li, M. Antonietti, Polycondensation of Boron- and Nitrogen-Codoped Holey Graphene Monoliths from Molecules: Carbocatalysts for Selective Oxidation. *Angew Chem Int Ed* 52, 4572-4576 (2013).
10. J. Liang, X. Du, C. Gibson, X. W. Du, S. Z. Qiao, N-Doped Graphene Natively Grown on Hierarchical Ordered Porous Carbon for Enhanced Oxygen Reduction. *Adv Mater* 25, 6226-6231 (2013).
11. H. G. Wang et al., Nitrogen-Doped Porous Carbon Nanosheets as Low-Cost, High-Performance Anode Material for Sodium-Ion Batteries. *Chemsuschem* 6, 56-60 (2013).
12. L. T. Qu, Y. Liu, J. B. Baek, L. M. Dai, Nitrogen-Doped Graphene as Efficient Metal-Free Electrocatalyst for Oxygen Reduction in Fuel Cells. *Acs Nano* 4, 1321-1326 (2010).
13. X. Y. Li et al., Silicon carbide-derived carbon nanocomposite as a substitute for mercury in the catalytic hydrochlorination of acetylene. *Nat Commun* 5, (2014).
14. Y. Zhao, R. Nakamura, K. Kamiya, S. Nakanishi, K. Hashimoto, Nitrogen-doped carbon nanomaterials as non-metal electrocatalysts for water oxidation. *Nat Commun* 4, art. 2390, (2013).
15. P. Nguyen et al., High thermal conductive beta-SiC for selective oxidation of $H_2S$: A new support for exothermal reactions. *Appl Catal B-Environ* 76, 300-310 (2007).
16. J. A. Zhang et al., Surface Chemistry and Catalytic Reactivity of a Nanodiamond in the Steam-Free Dehydrogenation of Ethylbenzene. *Angew Chem Int Edit* 49, 8640-8644 (2010).
17. J. Chlistunoff, RRDE and Voltammetric Study of ORR on Pyrolyzed Fe/Polyaniline Catalyst. On the Origins of Variable Tafel Slopes. *J Phys Chem C* 115, 6496-6507 (2011).
18. M.-M. Titirici, R. J. White, C. Falco, M. Sevilla, Black perspectives for a green future: hydrothermal carbons for environment protection and energy storage. *Energy Environ Sci* 5, 6796-6822 (2012).
19. C. O. Tuck, E. Perez, I. T. Horvath, R. A. Sheldon, M. Poliakoff, Valorization of Biomass: Deriving More Value from Waste. *Science* 337, 695-699 (2012).
20. D. Y. Zhang, Y. Hao, Y. Ma, H. X. Feng, Hydrothermal synthesis of highly nitrogen-doped carbon powder. *Appl Surf Sci* 258, 2510-2514 (2012).
21. K. G. Latham, G. Jambu, S. D. Joseph, S. W. Donne, Nitrogen Doping of Hydrochars Produced Hydrothermal Treatment of Sucrose in H2O, H2SO4, and NaOH. *Acs Sustain Chem Eng* 2, 755-764 (2014).
22. F. W. Lichtenthaler, A. Brust, E. Cuny, Sugar-derived building blocks. Part 26. Hydrophilic pyrroles, pyridazines and diazepinones from D-fructose and isomaltulose. *Green Chem* 3, 201-209 (2001).
23. F. W. Lichtenthaler, Unsaturated O- and N-heterocycles from carbohydrate feedstocks. *Accounts Chem Res* 35, 728-737 (2002).

The invention claimed is:

1. A method of preparing macroscopic composites made of a macroscopic support coated with a thin layer of highly nitrogen-doped mesoporous carbon phase, said method comprising:
   (a) providing an aqueous solution of (i) $(NH_4)_2CO_3$; (ii) a carbohydrate as carbon source, selected from aldose monosaccharides and glycosilated forms thereof, disaccharides and oligosaccharides or dextrine deriving from biomass conversion, and (iii) a carboxylic acid source selected from citric acid, and any other mono-, di-, tri-, and poly-carboxylic acid or their ammonium mono-, di-, tri- and poly-basic forms;
   (b) providing a macroscopic support made of carbon-, silicon- or aluminum-based material, or binary mixtures thereof; wherein the macroscopic support is a single object or an assembly of smaller objects, wherein the overall dimension of the support ranges from 0.1 μm to 100 cm in three orthogonal directions;
   optionally subjecting the maccroscopic support of step (b) to a passivation process comprising steps of:
      (a1) providing an aqueous solution of citric acid and a carbohydrate as carbon source, selected from aldose monosaccharides and glycosilated forms thereof, disaccharides and oligosaccharides;
      (b1) prior to step (c), immerging/soaking or impregnating the macroscopic support of step (b) in the aqueous solution of step (a1) for a suitable amount of time;
      (c1) optionally removing the immerged macroscopic support from the aqueous solution of step (a1) if an excess aqueous solution is used in step (b1);
      (d1) optionally subjecting the resulting macroscopic support to a gentle thermal treatment under air at low temperatures from 45 to 55° C.;
      (e1) subjecting the resulting macroscopic support to a first thermal treatment under air at moderate temperatures from 110-150° C.±5° C.; and
      (f1) subjecting the thermally treated macroscopic support to a second thermal treatment under inert atmosphere at higher temperatures from 600-800° C.±10° C.; thereby generating a macroscopic composite coated with a carbon layer;
   (c) immerging/soaking or impregnating the macroscopic support of step (b), or the passivated macroscopic support obtained in step (f1) when a passivation process is used, in the aqueous solution of step (a) for a suitable amount of time;
   (d) optionally removing the immerged macroscopic support from the aqueous solution of step (a) if an excess aqueous solution is used in step (c);
   (e') optionally subjecting the resulting macroscopic support to a gentle thermal treatment under air at low temperatures from 45 to 55° C.;
   (e) subjecting the resulting macroscopic support to a first thermal treatment under air at moderate temperatures from 110-150° C.±5° C.;
   (f) optionally subjecting the thermally treated macroscopic support to a second thermal treatment under air at higher temperatures:

from 400-500° C.±10° C., or
at 300° C.±10° C. for 2 to 4 hours;
thereby generating a macroscopic composite composed of a macroscopic support coated with a 20-200 nm thick layer of highly N-doped mesoporous carbonaceous material; wherein the N atom % in the mesoporous carbonaceous material is 25-40%; and (g) optionally subjecting the macroscopic composite obtained in step (e) or (f) to a third thermal treatment by heating it to a temperature ranging between 600 to 900° C.±10° C. under inert atmosphere;
thereby generating a macroscopic composite composed of a macroscopic support coated with a 10-100 nm thick layer of highly N-doped mesoporous carbonaceous material; wherein the N atom % in the mesoporous carbonaceous material is 2-35%;
wherein the method comprises at least one of steps (f) or (g).

2. The method of claim 1, wherein steps (c) through (f) are performed a first time and then repeated at least once prior to carrying out step (g).

3. The method of claim 1, wherein in the aqueous solution of step (a), $(NH_4)_2CO_3$ is present at a concentration ranging 1 to 8 mol/L; the carbohydrate carbon source is present at a concentration ranging from 1 to 5 mol/L; and the carboxylic acid source is present at a concentration ranging from 1 to 3 mol/L.

4. The method of claim 1, wherein the macroscopic support is made of a material selected from β-SiC or α-SiC or SiC-based supports, either pure or doped with foreign elements including $TiO_2$ or $SiO_2$, $Al_2O_3$, alumina, either pure or doped with foreign elements including $TiO_2$ or $SiO_2$; or carbon, each of which may be in the form of grains, flakes, rings, pellets, extrudates, beads or foam; or carbon nanotubes, carbon nanofibers, graphene or few-layer graphene.

5. The method of claim 1, wherein the macroscopic support is made of silica ($SiO_2$), SiC, alumina ($Al_2O_3$) or titania ($TiO_2$).

6. The method of claim 1, wherein the macroscopic support is made of silica ($SiO_2$), alumina ($Al_2O_3$) or titania ($TiO_2$), the method further comprising the passivation process.

7. The method of claim 1, wherein the immerging/soaking or impregnating step (c) is carried out for 1 to 10 minutes.

8. The method of claim 1, wherein the first thermal treatment step (e) is carried out for 1 to 10 hours.

9. The method of claim 1, wherein the second thermal treatment step (f) is carried out for 1 to 10 hours.

10. The method of claim 1, wherein the third thermal treatment step (g) is carried out for 1 to 10 hours.

11. The method of claim 1, wherein the N-doped carbonaceous material layer:
has an N atom contents of 1-40%;
has an average pore size of 2-50 nm; and
has a thickness of 5 to 200±5 nm.

* * * * *